US008524237B2

(12) United States Patent
Nicolaides et al.

(10) Patent No.: US 8,524,237 B2
(45) Date of Patent: *Sep. 3, 2013

(54) ANTIBODIES WITH IMMUNE EFFECTOR ACTIVITY AND THAT INTERNALIZE IN ENDOSIALIN-POSITIVE CELLS

(71) Applicant: Morphotek, Inc., Exton, PA (US)

(72) Inventors: Nicholas C. Nicolaides, Garnett Valley, PA (US); Luigi Grasso, Bryn Mawr, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,231

(22) Filed: Nov. 26, 2012

(65) Prior Publication Data

US 2013/0078242 A1     Mar. 28, 2013

Related U.S. Application Data

(63) Continuation of application No. 12/570,334, filed on Sep. 30, 2009, now Pat. No. 8,389,691, which is a continuation of application No. 11/410,472, filed on Apr. 24, 2006, now Pat. No. 7,615,372.

(60) Provisional application No. 60/674,344, filed on Apr. 22, 2005.

(51) Int. Cl.
*A61K 39/395* (2006.01)

(52) U.S. Cl.
USPC ....................................................... 424/156.1

(58) Field of Classification Search
None
See application file for complete search history.

(56) References Cited

U.S. PATENT DOCUMENTS

| 5,342,757 | A | 8/1994 | Garin-Chesa et al. |
| 5,437,865 | A | 8/1995 | Garin-Chesa et al. |
| 5,585,089 | A | 12/1996 | Queen et al. |
| 5,693,763 | A | 12/1997 | Codington et al. |
| 5,789,650 | A | 8/1998 | Lonberg et al. |
| 5,798,230 | A | 8/1998 | Bornkamm et al. |
| 5,811,522 | A | 9/1998 | Wallace et al. |
| 6,090,930 | A | 7/2000 | Wallace et al. |
| 6,146,894 | A | 11/2000 | Nicolaides et al. |
| 6,217,868 | B1 | 4/2001 | Wallace et al. |
| 6,261,535 | B1 | 7/2001 | Thorpe et al. |
| 6,391,302 | B1 | 5/2002 | Wallace et al. |
| 7,358,351 | B2 | 4/2008 | St. Croix et al. |
| 7,615,372 | B2 * | 11/2009 | Nicolaides et al. ........... 435/326 |
| 8,389,691 | B2 | 3/2013 | Nicolaides et al. |
| 2003/0124579 | A1 | 7/2003 | Mack et al. |
| 2004/0014058 | A1 | 1/2004 | Alsobrook et al. |
| 2004/0043928 | A1 | 3/2004 | Kekuda et al. |
| 2004/0048254 | A1 | 3/2004 | Olek et al. |
| 2004/0253606 | A1 | 12/2004 | Aziz et al. |
| 2005/0142138 | A1 | 6/2005 | St. Croix et al. |
| 2006/0121541 | A1 | 6/2006 | Grasso et al. |
| 2006/0127902 | A1 | 6/2006 | Madden et al. |
| 2006/0239911 | A1 | 10/2006 | Nicolaides et al. |
| 2007/0020271 | A1 | 1/2007 | Teicher et al. |
| 2007/0141066 | A1 | 6/2007 | Phillips et al. |
| 2007/0161022 | A1 | 7/2007 | Kim et al. |
| 2007/0292354 | A1 | 12/2007 | Port |
| 2008/0248034 | A1 | 10/2008 | Zhou et al. |
| 2008/0300170 | A1 | 12/2008 | Gelber et al. |
| 2009/0017030 | A1 | 1/2009 | St. Croix et al. |
| 2009/0175844 | A1 | 7/2009 | Nakamura et al. |
| 2009/0176656 | A1 | 7/2009 | Halloran |
| 2009/0203534 | A1 | 8/2009 | Hossain et al. |
| 2009/0239223 | A1 | 9/2009 | Gehrmann et al. |
| 2010/0062002 | A1 | 3/2010 | Madden et al. |
| 2010/0092470 | A1 | 4/2010 | Bhatt et al. |
| 2010/0092476 | A1 | 4/2010 | Hanash et al. |
| 2010/0136584 | A1 | 6/2010 | Bhatt et al. |
| 2010/0196426 | A1 | 8/2010 | Skog et al. |
| 2010/0260769 | A1 | 10/2010 | Sass et al. |

FOREIGN PATENT DOCUMENTS

| EP | 0 239 400 B1 | 8/1994 |
| JP | 08505764 | 6/1996 |
| WO | WO 90/07861 A1 | 7/1990 |
| WO | WO 94/11023 A1 | 5/1994 |
| WO | WO 95/24483 | 9/1995 |
| WO | WO 00/13575 A2 | 3/2000 |
| WO | WO 02/10217 A2 | 2/2002 |
| WO | WO 02/54856 A1 | 7/2002 |
| WO | WO 2004/078942 A2 | 9/2004 |

(Continued)

OTHER PUBLICATIONS

[Fundamental Immunology p. 242 (William E. Paul, M.D. ed., 3d ed; 1993)].*
Stancovski et al (PNAS, 88: 8691-8695, 1991).*
Jiang et al. (J. Biol. Chem. Feb. 11, 2005; 280 (6): 4656-4662).*
Zhang et al (BMC Cancer 11:pp. 1-9, 2011).*
European Patent Application No. 06769889.4: Examination Report dated Jun. 14, 2012, 4 pages.
Sun et al., "Antitumour Activity of a Chimeric Antibody Against the Leucocyte Antigen CD48," Cancer Immunology Immunotherapy, col. 48, No. 10, Jan. 3, 2000, 595-602, XP55025331.
Caldas et al, "Humanization of the Anti-CO18 Antibody 6.7: An Unexpected Effect of a Framework Residue in Binding to Antigen," Molecular Immunology, val. 39, No. 15, May 1, 2003, 941-952, XP55025334.

(Continued)

*Primary Examiner* — Brad Duffy
(74) *Attorney, Agent, or Firm* — Woodcock Washburn, LLP

(57) ABSTRACT

This invention relates to the use of monoclonal and polyclonal antibodies that specifically bind to and have the ability in the alternative to become internalized by cells expressing endosialin and to induce an immune effector activity such as antibody-dependent cellular cytotoxicity. The antibodies are useful in specific delivery of pharmacologic agents to endosialin-expressing cells as well as in eliciting an immune-effector activity particularly on tumor and neovascular cells and precursors. The invention is also related to nucleotides encoding the antibodies of the invention, cells expressing the antibodies; methods of detecting cancer and neovascular cells; and methods of treating cancer and neovascular disease using the antibodies, derivatives and fragments.

14 Claims, 3 Drawing Sheets

(56) References Cited

FOREIGN PATENT DOCUMENTS

| WO | WO 2005/086713 A2 | 9/2005 |
|---|---|---|
| WO | WO 2006/017759 A2 | 2/2006 |
| WO | WO 2006/029045 | 3/2006 |
| WO | WO 2006/060719 A2 | 6/2006 |
| WO | WO 2006/116451 A2 | 11/2006 |
| WO | WO 2008/021288 A2 | 2/2008 |
| WO | WO 2008/084331 A2 | 7/2008 |
| WO | WO 2008/097908 A2 | 8/2008 |
| WO | WO 2008/101118 A2 | 8/2008 |
| WO | WO 2008/122936 | 10/2008 |
| WO | WO 2009/021322 A1 | 2/2009 |
| WO | WO 2009/105549 A2 | 8/2009 |
| WO | WO 2009/120877 A2 | 10/2009 |
| WO | WO 2010/045714 | 4/2010 |
| WO | WO 2010/083252 | 7/2010 |

OTHER PUBLICATIONS

"FY2009 Product Creation Meeting, Dramatic Leap Plan 2011", Eisai Co., Ltd., Power Point Presentation, 121 pages, Dec. 18, 2009.
Asahara et al., "Endothelial progenitor cells for postnatal vasculogenesis", Am. J. Physiol. Cell Physiol., Sep. 2004, 287(3), C572-C579.
Bagley et al., "Endosialin/TEM 1/CD248 is a pericyte marker of embryonic and tumor neovascularization", Microvascular Research, Epub: Aug. 8, 2008, Nov. 2008, 76(3), 180-188.
Bagley et al., "Endothelial precursor cells as a model of tumor endothelium: characterization and comparison with mature endothelial cells", Cancer Res., Sep. 15, 2003, 63(18), 5866-5873.
Bagley et al., "Human endothelial precursor cells express tumor endothelial marker 1/endothesialin/CD248", Mol Cancer Ther., Aug. 2008, 7(8) 2536-2546.
Bagley et al., "Human mesenchymal stem cells from bone marrow express tumor endothelial and stromal markers", International Journal of Oncology, Mar. 2009, 34(3), 619-627.
Banapour et al., "Characterization and epitope mapping of a human monoclonal antibody reactive with the envelope glycoprotein of human immunodeficiency virus", J. Immunol., Dec. 15, 1987,139(12), 4027-4033.
Battle et al., "TEM1/Endosialin participates in cell-matrix and cell-cell adhesion interactions", abstract presented Apr. 16, 2007, Exhibit Hall, Los Angeles Convention Center.
Becker et al. "Tumor stroma marker endosialin (Tem1) is a binding partner of metastasis-related protein Mac-2 BPI90K", The FASEB Journal, Aug. 2008, Epub: May 19, 2008, 22(8):3059-3067.
Bendayan et al, "Possibilities of false immunocytochemical results generated by the use of monoclonal antibodies: the example of the anti-proinsulin antibody" Sep. 1995, J Histochem Cytochem, 43(9):881-886.
Betsholtz, "Insight into the physiological functions of PDGF through genetic studies in mice", Cytokine Growth Factor Rev., Aug. 2004, 15(4), 215-228.
Boerner et al., "Production of antigen-specific human monoclonal antibodies from in vitro-primed human splenocytes", J. of Immunol., Jul. 1, 1991, 147(1), 86-95.
Bohring et al., "Expression of novel surface antigens on early hematopoietic cells", Ann. N.Y. Acad. Sci., Apr. 30, 1999, 872, 25-38, Discussion 38-39.
Bost et al, "Antibodies against a peptide sequence within the HIV envelope protein crossreacts with human interleukin-2", Aug.-Oct. 1988, Immunol Investigation, 17 (6&7), 577-586.
Bowie etal, "Deciphering the message in protein sequences: tolerance to amino acid substitutions", Science, Mar. 1990,257,1306-1310.
Brady et al., "Human endosialin (tumor endothelial marker 1) is abundantly expressed in highly malignant and invasive brain tumors", J Neuropathol. Exp. Neural., Dec. 2004, 63(12),1274-1283.
Carson-Walter et al., "Cell surface tumor endothelial markers are conserved in mice and humans", Cancer Res., Sep. 15, 2001, 61(18), 6649-6655.
Carson-Walter et al., "Characterization of TEM1/endosialin in human and murine brain tumors", BMC Cancer, 2009, Epub: Nov. 30, 2009, 9, 417, 1-13.
Chothia et al., "Canonical Structures for the Hypervariable Regions of Immunglobulins", J. Mol. Bioi., Aug. 20, 1987, 196(4), 901-917.
Choudhury et al., "c-Src couples PI 3 kinase/Akt and MAPK signaling to PDGF-induced DNA synthesis in mesangial cells", Cell Signal., Nov. 2006, 18(11), 1854-1864.
Christian et al., "Endosialin (Tem1) is a marker of tumor-associated myofibroblasts and tumor vessel-associated mural cells", The American Journal of Pathology, Epub: Jan. 10, 2008, Feb. 2008, 172(2), 486-494.
Christian et al., "Molecular cloning and characterization of endosialin, a C-type lectin-like cell surface receptor of tumor endothelium", J. Bioi. Chem., Mar. 9, 2001, Epub: Nov. 17, 2000, 276(10), 7408-7414.
Christian et al., "Molecular cloning and characterization of EndoGiyx-1, an EMILIN-like multisubunit glycoprotein of vascular endothelium", J. Bioi. Chem., Dec. 21, 2001, Epub: Sep. 14, 2001, 276(51), 48588-48595.
Cole et al., "The EBV-hybridoma technique and its application to human lung cancer", Monoclonal Antibodies and Cancer Therapy (vol. 27, UCLA Symposia on Molecular and Cellular Biology, New Series) (eds. R.A. Reisfeld and S. Sell), Alan R. Liss, Inc. N.Y., 1985, 77-96.
Conejo-Garcia et al., "Vascular leukocytes contribute to tumor vascularization", Blood, Jan. 15, 2005, Epub: Sep. 9, 2004, 105(2), 679-681.
Das et al., "Retinal and choroidal angiogenesis: pathophysiology and strategies for inhibition", Prog. Retin. Eye Res., Nov. 2003, 22(6), 721-748.
Davies et al., "Levels of expression of endothelial markers specific to tumour-associated endothelial cells and their correlation with prognosis in patients with breast cancer", Clin Exp Metastasis, Nov. 2, 2004, 21(1), 31-37.
Dhanabal, "Anti-angiogenic therapy as a cancer treatment paradigm", Curr. Med. Chem. Anti-Canc. Agents, Mar. 2005, 5(2), 115-130.
Dillman, "Monoclonal Antibodies for Treating Cancer", Ann. Internal Med., Oct. 1, 1989, 111(7), 592-603.
Dolznig et al., "Characterization of Cancer Stroma Markers: In silica analysis of an mRNA expression database for fibroblast activation protein and endosialin" Cancer Immunity, Aug. 3, 2005, 5, 10.
Florell et al., "Preservation of RNA for functional genomic studies: a multidisciplinary tumor bank protocol", Mod. Pathol., Feb. 2001, 14(2), 116-128.
Foote et al., "Antibody Framework Residues Affecting the Conformation of the Hypervariable Loops", J. Mol. Bioi., Mar. 20, 1992, 224(2), 487-499.
Galiano et al., "Topical vascular endothelial growth factor accelerates diabetic wound healing through increased angiogenesis and by mobilizing and recruiting bone marrow-derived cells", Am. J. Pathol., Jun. 2004, 164(6), 1935-1947.
Garmestani et al., "Synthesis and evaluation of a macrocyclic bifunctional chelating agent for use with bismuth radionuclides", Nucl. Med. Bioi., May 2001, 28(4), 409-418.
GenBank Accession No. AF279142, "*Homo sapiens* tumor endothelial marker 1 precursor (TEM1) mRAN, complete cds", Aug. 23, 2000.
Geng et al, Cellular and molecular immunology (China), 2006, 3 (6), p. 439-43.
Gerhardt & Betsholtz, "Endothelial-pericyte interactions in angiogenesis", Cell Tissue Res, Oct. 2003, Epub: Jul. 22, 2003, 314(1), 15-23.
Hanahan et al., "The hallmarks of cancer", Cell, Jan. 7, 2000, 100(1), 57-70.
Hauck et al., "Focal adhesion kinase facilitates platelet-derived growth factor-BB-stimulated ERK2 activation required for chemotaxis migration of vascular smooth muscle cells", J Bioi. Chem., Dec. 29, 2000, 275(52), 41092-41099.
Heldin & Westermark, "Mechanism of action and in vivo role of platelet-derived rowth factor", Physiol Rev., Oct. 1999, 79(4), 1283-1316.

Hellstrom et al., "Role of PDGF-B and PDGFR-beta in recruitment of vascular smooth muscle cells and pericytes during embryonic blood vessel formation in the mouse", Development, Jun. 1999, 126(14), 3047-3055.

Hollenbeck et al., "Type I collagen synergistically enhances PDGF-induced smooth muscle cell proliferation through pp60src-dependent crosstalk between the alpha2beta1 integrin and PDGFbeta receptor", Biochem. Biophys. Res Commun., Dec. 3, 2004, 325(1), 328-337.

Homandberg, "Potential regulation of cartilage metabolism in osteoarthritis by fibronectin fra ments", Front Biosci., Oct. 15, 1999, 4:D713-730.

Huang et al., "Construction of representative immunoglobulin variable region eDNA libraries from human peripheral blood lymphocytes without in vitro stimulation", J. Immunol. Methods, Aug. 9, 1991, 141(2), 227-236.

Huber et al., "Expression of stromal cell markers in distinct compartments of human skin cancers", J Cutan Pathol, Feb. 2006, 33(2), 145-155.

Hynes, "Integrins: Bidirectional, Allosteric Signaling Machines", Cell, Sep. 20, 2002, 110(6), 673-687.

Jones et al., "Replacing the complementarity-determining regions in a human antibody with those from a mouse", Nature, May 29-Jun. 4, 1986, 321(6069), 522-525.

Kala et al., "Phage Displayed Antibodies to Heat Stable Alkaline Phosphatase: Framework Region as a Determinant of Specificity", J. Biochem., Oct. 2002, 132(4), 535-541.

Khazaeli et al., "Human immune response to monoclonal antibodies", J. of Immunother., Jan. 1994, 15(1), 42-52.

Kikuchi et al., "Apoptosis inducing bivalent single-chain antibody fragments against CD47 showed antitumor potency for multiple myeloma", Leuk. Res., Apr. 2005, Epub: Dec. 18, 2004, 29(4), 445-450.

Kohler et al., "Continuous cultures of fused cells secreting antibody of predefined specificity", Nature, Aug. 7, 1975, 256(5517), 495-497.

Kozbor et al., "The production of monoclonal antibodies from human lymphocytes", Immunol. Today, Mar. 1983, 4(3), 72-79.

Kreitman et al., "Immunotoxins for targeted cancer therapy", Adv. Drug Del. Rev., Apr. 6, 1998, 31(1-2), 53-88.

Kuntz, "Structure-based strategies for drug design and discovery", Science, Aug. 21, 1992, 257(5073), 1078-1082.

Kurosawa et al., "Genomic analysis of a murine cell-surface sialomucin, MGC-24/CD163", Eur. J. Biochem., Oct. 1, 1999, 265(1), 466-472.

Kusano et al., "Immunocytochemical study on internalization of anti-carbohydrate monoclonal antibodies", Anticancer Res., Nov.-Dec. 1993, 13(6A), 2207-2212.

Kyriakos et al., "The fate of antibodies bound to the surface of tumor cells in vitro", Cancer Research, Feb. 15, 1992, 52(4), 835-842.

Labat-Robert, "Fibronectin in malignancy Effect on aging", Semin. Cancer Bioi., Jun. 2002, 12(3):187-195.

Leveen et al., "Mice deficient for PDGF B show renal, cardiovascular, and hematological abnormalities", Genes Dev., Aug. 1994, 8(16), 1875-1887.

Li et al., "Differential effects of imatinib on PDGF-induced proliferation and PDGF receptor signaling in human arterial and venous smooth muscle cells", J Cell Biochem., Dec. 15, 2006, 99(6), 1553-1563.

Lindahl et al., "Pericyte loss and microaneurysm formation in PDGF-B-deficient mice", Science, Jul. 11, 1997, 277(5323), 242-245.

MacFadyen et al., "Endosialin (TEM1, CD248) is a marker of stromal fibroblasts and is not selectively expressed on tumour endothelium", FEBS letters, Epub: Apr. 7, 2005, May 9, 2005, 579(12), 2569-2575.

MacFadyen et al., "Endosialin is expressed on stromal fibroblasts and CNS pericytes in mouse embryos and is downregulated during development", Gene Expression Patterns, Epub: Jul. 27, 2006, Jan. 2007, 7(3), 363-369.

Magnusson & Mosher, "Fibronectin: structure, assembly, and cardiovascular implications.", Arterioscler. Thromb. Vasc. Bioi., Sep. 1998, 18(9), 1363-1370.

Marks et al., "By-passing immunization. Human antibodies from V-gene libraries displayed on phage", J. Mol. Bioi., Dec. 5, 1991, 222(3), 581-597.

Marty et al., "Isolation and characterization of a scFv antibody specific for tumor endothelial marker 1 (TEM1), a new reagent for targeted tumor therapy", Cancer Letts., Apr. 28, 2006, Epub: Jun. 13, 2005, 235(2), 298-308.

McKeown-Longo & Mosher, "Binding of plasma fibronectin to cell layers of human skin fibroblasts.", J. Cell Bioi., Aug. 1983, 97(2), 466-472.

McKeown-Longo & Mosher, "Interaction of the 70,000-mol-wt amino-terminal fragment of fibronectin with the matrix-assembly receptor of fibroblasts", J. Cell Bioi., Feb. 1985, 100(2), 364-374.

Miller et al, "Ligand binding to proteins: the binding landscape model", Protein Sci., Oct. 1997, 6(10), 2166-2179.

Millette et al., "Platelet-derived growth factor-BB transactivates the fibroblast growth factor receptor to induce proliferation in human smooth muscle cells", Trends Cardiovasc. Med., Jan. 2006, 16(1), 25-28.

Modzelewski et al., "Isolation and Identification of Fresh Tumor-derived Endothelial Cells from a Murine RIF-1 Fibrosarcoma", Cancer Res., Jan. 15, 1994, 54(2), 336-339.

Morea et al., "Conformations of the Third Hypervariable Region in the VH Domain of Immunoglobulins", J. Mol. Bioi., Jan. 16, 1998, 275(2), 269-294.

Morrison et al., "Chimeric human antibody molecules: mouse antigen-binding domains with human constant region domains", Proc. Natl. Acad. Sci. USA, Nov. 1984, 81(21), 6851-6855.

Naito et al., "Ets-1 is an early response gene activated by ET-1 and PDGF-BB in vascular smooth muscle cells", Am. J Physiol, Feb. 1998, 274(2 pt. 1), C472-C480.

Nanda et al., "Tumor Endothelial Marker 1 (TEM1) Functions in the Growth and Progression of Abdominal Tumors", PNAS, Feb. 28, 2006, Epub: Feb. 21, 2006, 103(9), 3351-3356.

Niwa et al., "Defucosylated chimeric anti-CC chemokine receptor 4 IgG1 with enhanced antibody-dependent cellular cytotoxicity shows potent therapeutic activity to T-cellleukemia and lymphoma", Cancer Res., Mar. 15, 2004, 64(6), 2127-2133.

Ohradanova et al., "Hypoxia upregulates expression of human endosialin gene via hypoxia-inducible factor 2", Br J Cancer, Oct. 21, 2008, Epub: Sep. 23, 2008, 99(8):1348-1356.

Opaysky et al., "Molecular characterization of the mouse Tem1/endosialin gene regulated by cell density in vitro and expressed in normal tissues in vivo", The Journal of Biological Chemistry, Oct. 19, 2001, Epub: Aug. 6, 2001, 276(42), 38795-38807.

Orlandi et al., "Cloning immunoglobulin variable domains for expression by the polymerase chain reaction", Proc. Natl. Acad. Sci. USA, May 1989, 86(10), 3833-3837.

Paleolog et al., "Angiogenesis in arthritis: role in disease pathogenesis and as a potential therapeutic target", Angiogenesis, Dec. 1998, 2(4), 295-307.

Panka et al., "Variable region framework differences result in decreased or increased affinity of variant anti-digoxin antibodies", Proc. Natl. Acad. Sci. USA, May 1988, 85(9), 3080-3084.

Paul et al., "Selection of Tumor-Specific Internalizing Human Antibodies from Phage Libraries", Journal of Molecular Biology, Apr. 17, 2000, 301(5), 1149-1161.

Persson et al., "Generation of diverse high-affinity human monoclonal antibodies by repertoire cloning", Proc. Nat. Acad. Sci. USA, Mar. 15, 1991, 88(6), 2432-2436.

Peters et al., "Contribution of bone marrow-derived endothelial cells to human tumor vasculature", Nat. Med., Mar. 3, 2005, Epub: Feb. 20, 2005, 11(3), 261-262.

Presta, "Antibody engineering", Curr. Op. Biotechnol., Aug. 1992, 3(4), 394-398.

Queen et al., "A humanized antibody that binds to the interleukin 2 receptor", Proc. Nat. Acad. Sci. USA, Dec. 1989, 86(24), 10029-10033.

Reichmann et al., "Reshaping human antibodies for therapy", Nature, Mar. 24, 1988, 332(6162), 323-327.

Rettig et al., "Identification of endosialin, a cell surface glycoprotein of vascular endothelial cells in human cancer", Proc Natl. Acad Sci USA, Nov. 15, 1992, 89(22), 10832-10836.

Rmali et al., "Prognostic values of tumor endothelial markers in patients with colorectal cancer", World J Gastroenterol, Mar. 7, 2005, 11(7), 1283-1286.

Roger, et al, "Several epitopes of p85 glycoprotein (CDw44) are dependent on intact disulphide bonds. Isolation of cDNA clones requires a polyclonal antibody raised against the reduced protein" Aug. 1988, Bioscience Reports, 8(4): 359-368.

Rouleau et al., "Endosialin protein expression and therapeutic target potential in human solid tumors: sarcoma versus carcinoma", Clin Cancer Res, 2008, 14(22): 7223-7226.

Rudikoff et al, "Single amino acid substitution altering antigen-binding specificity" PNAS, USA, Mar. 1982, 79(6),1979-83.

Ruoslahti et al., "Alignment of biologically active domains in the fibronectin molecule", J. Bioi. Chem., Jul. 25, 1981, 256(14), 7277-7281.

Rupp et al., "Laser capture microdissection of epithelial cancers guided by antibodies against fibroblast activation protein and endosialin", Diagnostic Mol Pathol, 2006, 15(1):35-42.

Rupp et al., "Mouse endosialin, a C-type lectin-like cell surface receptor: expression during embryonic development and induction in experimental cancer neoanQio wnesis", Cancer Immun, Jul. 31, 2006, 6, 10.

Scott et al., "Immunological effects of chimeric anti-GD3 monoclonal antibody KM871 in patients with metastatic melanoma", Cancer Immun., Feb. 22, 2005, 5(3), 1-12.

SIGMA® Product Information, Product No. F 0162, Fibronectin Proteolytic Fragment, 45 kDa from human plasma.

SIGMA® Product Information, Product No. F 0287, Fibronectin Proteolytic Fragment, 70 kDa from human plasma.

SIGMA® Product Information, Product No. F 9911, Fibronectin Proteolytic Fragment, 30 kDa from human plasma.

Song et al., "PDGFRbeta+ perivascular progenitor cells in tumours regulate pericyte differentiation and vascular survival", Nat Cell Bioi, Sep. 2005, Epub: Aug. 21, 2005, 7(9), 870-879.

Soriano, "Abnormal kidney development and hematological disorders in PDGF beta-receptor mutant mice", Genes Dev., Aug. 15, 1994, 8(16), 1888-1896.

St. Croix et al., "Genes expressed in human tumor endothelium", Science, Aug. 18, 2000, 289(5482), 1197-1202.

St. Croix et al., in MPSRCH search result, 2008, US-1 1.410.472.2.rag.RESULT 1, and US-1 1.41 0.472.1 .rag. RESULT 2, pp. 1-5.

Sun et al., "Antitumor activity of a chimeric antibody against the leucocyte antigen CD48", Cancer Immunol. Immunther., Jan. 2000, 48(10), 595-602.

Tempest et al., "Reshaping a human monoclonal antibody to inhibit human respiratory syncytial virus infection in vivo", Biotechnology, Mar. 1991, 9(3), 266-271.

Tomasini-Johansson et al., "The N-terminal 70-kDa fragment of fibronectin binds to cell surface fibronectin assembly sites in the absence of intact fibronectin", Matrix Bioi., Jul. 2006, Epub: Mar. 3, 2006, 25(5), 282-293.

Tomkowicz et al., "Interaction of endosialin.tem1 with extracellular matrix proteins medicates cell adhesion and migration", Proceedings of the Natl. Acad. of Sci, USA, Nov. 13, 2007, Epub: Nov. 6, 2007, 104(46), 17965-17970.

Trail et al., "Monoclonal antibody drug immunoconjugates for targeted treatment of cancer", Cancer Immunology, May 2003, Epub: Jan. 16, 2003, 52(5), 328-337.

Verhoeyen et al., "Reshaping human antibodies: grafting an antilysozyme activity", Science, Mar. 25, 1988, 239(4847), 1534-1536.

Virgintino et al., "An intimate interplay between precocious, migrating pericytes and endothelial cells governs human fetal brain angiogenesis", Angiogenesis, Epub: Jan. 17, 2007, 2007, 10(1), 35-45.

Watt et al., "CD164, a novel sialomucin on CD34(+) and erythroid subsets, is located on human chromosome 6q21", Blood, Aug. 1, 1998, 92(3), 849-866.

Watt et al., "CD164-a novel sialomucin on CD34+ cells", Leuk. Lymphoma., Mar. 2000, 37(1-2), 1-25.

Wierzbicka-Patynowski & Schwarzbauer, "The ins and outs of fibronectin matrix assembly", J. Cell Sci., Aug. 15, 2003, 116(Part 16), 3269-3276.

Wilkinson-Berka, "Vasoactive factors and diabetic retinopathy: vascular endothelial growth factor, cycoloxygenase-2 and nitric oxide", Curr. Pharm. Des., 2004, 10(27), 3331-3348.

William E. Paul, ed., 3rd ed. 1993, Fundamental Immunology, p. 242.

Wolff et al., "Monoclonal antibody homodimers: enhanced antitumor activity in nude mice", Cancer Res., Jun. 1, 1993, 53(11), 2560-2565.

Yancopoulos et al., "Vascular-specific growth factors and blood vessel formation", Nature, Sep. 14, 2000, 407(6801), 242-248.

Zafiropoulos et al., "Induction of antigen-specific isotype switching by in vitro immunization of human naYve B lymphocytes", J. of Immunological Methods, Jan. 15, 1997, 200(1-2), 181-190.

Zannettino et al., "The sialomucin CD164 (MGC-24v) is an adhesive glycoprotein expressed by human hematopoietic progenitors and bone marrow stromal cells that serves as a potent negative regulator of hematopoiesis", Blood, Oct. 15, 1998, 92(8), 2613-2628.

* cited by examiner

Figure 2A
Figure 2B
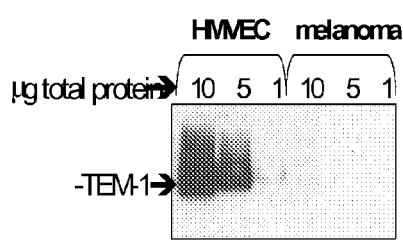
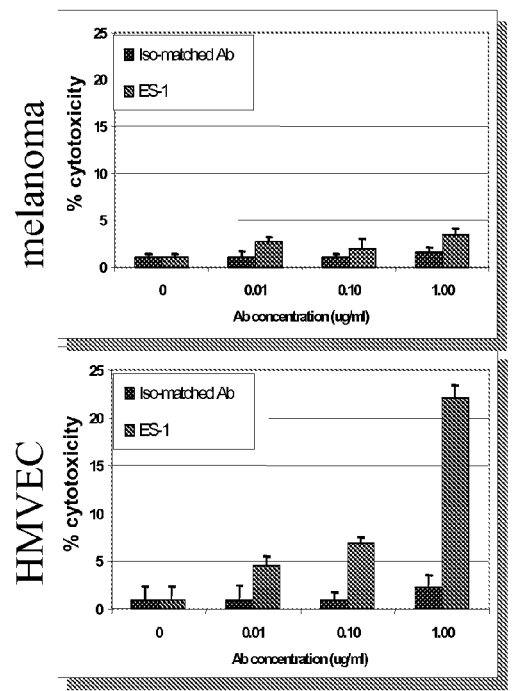

ANTIBODIES WITH IMMUNE EFFECTOR ACTIVITY AND THAT INTERNALIZE IN ENDOSIALIN-POSITIVE CELLS

CROSS-REFERENCE TO RELATED APPLICATION

This is a continuation of U.S. application Ser. No. 12/570,334, now U.S. Pat. No. 8,389,691, filed Sep. 30, 2009, which is a continuation application of U.S. application Ser. No. 11/410,472, now U.S. Pat. No. 7,615,372, filed Apr. 24, 2006, which claims benefit of U.S. Provisional Application 60/674,344, filed Apr. 22, 2005. Each of these applications is incorporated herein by reference in its entirety.

FIELD OF THE INVENTION

This invention relates to the use of monoclonal and polyclonal antibodies that specifically bind to and alternatively become internalized by cells expressing or bearing endosialin ("endosialin-positive cells") or induce an immune effector activity such as antibody-dependent cellular cytotoxicity. The antibodies are useful in specific delivery of pharmacologic agents to endosialin-positive cells as well as in eliciting an immune-effector activity particularly on endosialin-positive cells including but not limited to neovascular cells, endothelial precursors, tumor, tumor stromal and dysplastic cells. The invention is also related to cells expressing the monoclonal antibodies, polyclonal antibodies, antibody derivatives, such as chimeric and humanized monoclonal antibodies, antibody fragments, methods of detecting endosialin-positive cells, and methods of treating cancer and neovascular disease with the antibodies of the invention.

BACKGROUND OF THE INVENTION

Angiogenesis is a regulated process involving the formation of new blood vessels. It plays an essential role in normal growth, embryonic development, wound healing, and other physiological processes (Yancopoulos et al. (2000) *Nature* 407(6801):242-8). Moreover, de novo angiogenesis is involved in several disease states including cancer, where the formation of new "embryonic-like" blood vessels (referred to as neovascularization herein) appear that differ from normal vasculature with regards to structure and function (Hanahan and Weinberg (2000) *Cell* 100(1):57-70). A number of in vivo and in vitro studies have demonstrated biological differences between normal and disease-associated vasculature as determined using various model systems of angiogenesis offering the ability to develop novel anti-angiogenic compounds that can selectively inhibit vessel formation of the embryonic-type, tumor-associated endothelial-type for therapy of neovascular disease. In light of these opportunities for therapy, an intense search for potential targets that can specifically inhibit tumor and other neovascular disease-associated endothelial cell growth and function is ongoing. In an attempt to identify such targets, strategies have been designed to identify cell surface antigens of tumor stroma as well as isolate specific proteins or RNA that are expressed in neovascular endothelial cells (Rettig et al. (1992) *Proc Natl. Acad Sci USA* 89(22):10832-6; St. Croix et al. (2000) *Science* 289:1197-1202). These strategies have identified a cell surface protein that appears to be specifically expressed in neovascular endothelial cells called endosialin (or tumor endothelial marker 1, TEM1). The use of antibodies in immunohistochemistry studies of malignant tissues have found good expression of endosialin in a number of neovascular endothelial cells in malignant tissues, tumor stromal cells, and putative endothelial leukocytes [(Brady et al. (2004) Human endosialin (tumor endothelial marker 1) is abundantly expressed in highly malignant and invasive brain tumors. *J. Neuropathol Exp Neurol.* 63:1274-83; Rettig et al. (1992); Conejo-Garcia et. al. (2005) Vascular leukocytes contribute to tumor vascularization. *Blood* 105:679-81)] while expression in cell lines derived from embryonic-like endothelial cultures such as but not limited to HUVEC (Human Umbilical Vein Endothelial Cells) or HMVEC-(Neonatal Dermal Microvascular Endothelial Cells) is limited (available online through Cambrex Corp.). Analysis of antibodies that can bind to endosialin have identified a set of cells that express this antigen in endothelial cell cultures as well as a subset of dendritic-like cells in normal tissue of patients. Recently it has been shown that leukocytes contain cells that can form endothelial cells in vessels of tumors, supporting the use of antibodies in targeting these endosialin-positive cell types for therapy (Peters et al. (2005) Contribution of bone marrow-derived endothelial cells to human tumor vasculature. *Nat. Med.* 11:261-262).

Neovascularization is associated with a number of disease states. In cancer it is believed that neovascularization is important to supply tumors with blood. In non-oncology diseases such as retinopathy and macular degeneration, uncontrolled neovascularization causes loss of sight (Wilkinson-Berka (2004) *Curr Pharm Des.* 10(27):3331-48; Das and McGuire (2003) *Prog Retin Eye Res.* 22(6):721-48). Moreover, several reports have identified a role of neovascularization in inflammatory disease (Paleolog and Miotla (1998) *Angiogenesis* 2(4):295-307). Methods to better define the embryonic-like endothelial and precursor cells associated with these disease states will lead to the development of novel drugs to treat these diseases. The development of antibodies that can specifically target endothelial cells associated with cancer or neovascular disease (age-related macular degeneration, retinopathy, inflammation, etc.) offers the ability to treat these diseases.

A difficult problem in effective antiangiogenic and proangiogenic therapy is the inability to specifically target and kill or suppress the action of these cells via pharmaceutical compounds. An approach to get better specificity to treat cancer or neovascular disease is the use of antibodies that can target specific antigens expressed in cancer or neo-endothelial cells or precursors that are not expressed or are expressed at a lower level on normal cells. These targets can be exploited using antibodies to kill antigen-bearing cells by inhibiting the biological activity of the antigen, eliciting an immune effector function by complement-dependent cytotoxicity (CDC) and/or antibody-dependent cellular cytotoxicity (ADCC); or by delivering immuno- or radio-conjugates that, when delivered to the antigen-bearing cells, specifically kill the target cell. Finding antibodies that can specifically bind to and effectively kill antigen-bearing cells involved in tumorigenesis and neovascular-associated disease, such as inflammation, age-related macular degeneration, and retinopathy, has proven difficult for many biological compounds (Dhanabal (2005) Anti-angiogenic therapy as a cancer treatment paradigm *Curr Med Chem Anti-Canc Agents* 5:115-30). This has been due in part to the inability to get robust killing due to lack of immune-effector activity or lack of efficient internalization of antibodies carrying immunotoxins.

In 1992, Rettig et al. described monoclonal antibodies that recognize antigens on vessels within various cancer types (Rettig et al. (1992) *Proc Natl. Acad Sci USA* 89(22):10832-6). One of these was designated FB5, which recognizes a ~100 kDa protein on the surface of a neuroblastoma cell line, LA1-5s. FB5 is a murine IgG1 antibody that binds to endosialin and has been shown to recognize endothelial cells associated with a variety of different cancer types. Structural evaluation classified endosialin as a C-type lectin-like protein composed of five globular extracellular domains (including a C-type lectin domain, one domain with similarity to the Sushi/ccp/scr pattern, and three EGF repeats). The protein also contains a mucin-like region, a transmembrane segment, and a short cytoplasmic tail. The protein appears to be a glycoprotein. Carbohydrate analysis shows that the endosialin core protein has an abundance of sialylated, O-linked oligosaccharides with similarities to sialomucin-like molecules. Subsequent work combined the complementarity determining regions (CDR) of the mouse FB5 onto a human IgG1 backbone to create a humanized antibody that is able to also bind to vessels within malignant tissues and a subset of cells in HMVEC cultures. U.S. Pat. No. 5,342,757 describes the FB5 antibody that binds to a ~100 kDa protein.

Endosialin offers an opportunity to specifically target cancer and neovascular disease. Provided herein are in-out antibodies that can, in the alternative, internalize in endosialin-positive cells (e.g., for delivery of toxic conjugates) and elicit a cytotoxic effect via immune effector activity. The antibodies of the invention provide effective antibody therapies for cancer, neovascular-associated diseases such as but not limited to macular degeneration (e.g., age-related macular degeneration), retinopathy, and inflammation, and other conditions associated with endosialin.

SUMMARY OF THE INVENTION

The invention provides endosialin-specific antibodies that alternatively elicit a robust immune-effector function or internalize in endosialin-positive cells, referred to here as in-out anti-endosialin antibodies. As used herein, "in-out antibodies" ("in-out Abs") refer to antibodies that can alternatively elicit an immune effector activity and internalize within an antigen-presenting cell by binding to target antigen. Without wishing to be bound by any particular theory, it is believed that in-out Abs bind to the cell surface of an antigen-bearing cell and internalize after a period of time unless engaged by immune effector cells or biochemicals that are recruited to the antigen-antibody-bearing cell. Antibodies that are able to elicit an immune effector effect such ADCC or CDC and internalize have been previously described (Wolff et al. Monoclonal antibody homodimers: enhanced antitumor activity in nude mice. *Cancer Res.* 1993 Jun. 1; 53:2560-5), however, it is not obvious that in-out antibodies can be developed against any antigen or epitope (Kusano et al. Immunocytochemical study on internalization of anti-carbohydrate monoclonal antibodies. *Anticancer Res.* 1993 November-December; 13(6A):2207-12). In-out antibodies that can target endosialin have not been described previously. Endosialin-specific antibodies have been previously described but such antibodies are not known to internalize and to elicit an immune effector function on endosialin-bearing cells (Rettig et al. 1992; Brady et al. 2004). Antibodies that can target cell surface antigens do not always elicit an immune effector function upon binding to the cell surface antigen (Niwa et al. Defucosylated chimeric anti-CC chemokine receptor 4 IgG1 with enhanced antibody-dependent cellular cytotoxicity shows potent therapeutic activity to T-cell leukemia and lymphoma. *Cancer Res.* 64:2127-33, 2004; Kikuchi et al. Apoptosis inducing bivalent single-chain antibody fragments against CD47 showed antitumor potency for multiple myeloma. *Leuk Res.* 29:445-50, 2005; Scott et al. Immunological effects of chimeric anti-GD3 monoclonal antibody KM871 in patients with metastatic melanoma. *Cancer Immun. Feb.* 22; 5:3, 2005). Provided herein are antibodies that bind to the cell surface antigen endosialin and alternatively elicit an immune effector activity (such as ADCC or CDC) and internalize within antigen-bearing cells. These antibodies and derivatives thereof are useful for therapy for cancer and neovascular disease.

The invention provides in-out antibodies that specifically bind to endosialin. In some embodiments, the antibodies bind antigen with greater affinity and/or avidity than FB5. In some embodiments the in-out antibodies of the invention bind the same epitope, for example a conformational epitope, as that bound by FB5. In other embodiments, the in-out antibodies of the invention bind a different epitope as that bound by FB5.

The antibodies of the invention may be chimeric, including, but not limited to human-mouse chimeric antibodies. The antibodies of the invention may also be humanized. The antibodies of the invention may also be fully human. The invention also provides: hybridoma cells that express the antibodies of the invention; polynucleotides that encode the antibodies of the invention; vectors comprising the polynucleotides that encode the antibodies of the invention; and expression cells comprising the polynucleotides of the invention, referred to as transfectomas.

The invention also provides methods of producing an in-out antibody that specifically binds to endosialin. Some methods comprise the step of culturing the transfectoma or hybridoma cell that expresses an antibody of the invention. The antibody-producing cells of the invention may be bacterial, yeast, insect cells, and animal cells, preferably, mammalian cells.

The invention further provides methods of inhibiting the growth of endosialin-positive cells. In some embodiments, such methods comprise administering to a patient with such cells a composition comprising an in-out antibody that specifically binds to endosialin. The methods may be used for the treatment of, for example, inflammatory disease, other neovascular disease, eye diseases including age-related macular degeneration and retinopathy, cancer and various dysplastic conditions, such as, but not limited to ovarian, breast, colorectal, renal and lung cancer. In preferred embodiments, the patients are human patients. In some embodiments, the antibodies are conjugated to one or more chemotherapeutic agents such as, but not limited to radionuclides, toxins, and cytotoxic and cytostatic agents. In other embodiments the antibodies are used in combination with one or more chemotherapeutic agents. In-out antibodies can be administered as a single agent, as a conjugated or unconjugated antibody, or in combination with the conjugated or unconjugated forms or another therapeutic agent.

Previous attempts to develop in-out antibodies that can specifically target endosialin have not been reported. Here we describe the development of in-out antibodies that can internalize in endosialin-positive cells and, if not internalized, elicit a cytotoxic effect via an immune effector activity.

Other features and advantages of the invention will be apparent from the detailed description and examples that follow.

BRIEF DESCRIPTION OF THE DRAWINGS

FIG. 2 shows the ability of ES-1 to elicit ADCC immune effector activity. ES-1 elicits a robust ADCC activity. FIG. 2A illustrates non-denaturing Western blot of HMVEC cells showing the ability of ES-1 antibody to bind to endosialin while null melanoma cells were negative. The lower panel of FIG. 2B shows target HMVEC cells (referred to as target) incubated with human peripheral blood lymphocytes (PBLs) alone (0 lane); or with increasing amount of with ES-1 (right bar) or control Ig (normal IgG-left bar). Cell cultures were assayed for killing by monitoring for lactate dehydrogenase (LDH) release that occurs upon cell lysis. As shown, ES-1 has ADCC activity on endosialin-expressing cells. The upper panel of FIG. 2B shows human melanoma cells that are null for endosialin incubated with human PBLs alone (0 lane); or with increasing amount of with ES-1 (right bar) or control Ig (normal IgG-left bar). Cell cultures were assayed for killing by monitoring for lactate dehydrogenase (LDH) release that occurs upon cell lysis. As shown, ES-1 has no ADCC activity on endosialin null cells.

FIG. 3 shows the ability of ES-1 linked to saporin (diamond) to kill cells in contrast to ES-1 antibody alone (not shown) while an isotype control antibody did not kill cells in conjugated toxin form (square). As control, cells not expressing endosialin were used and showed that ES-1 has no toxic effect in conjugated or unconjugated form (not shown). These data support the findings that ES-1 internalizes in endosialin-bearing cells.

DETAILED DESCRIPTION OF ILLUSTRATIVE EMBODIMENTS

Figure 1:
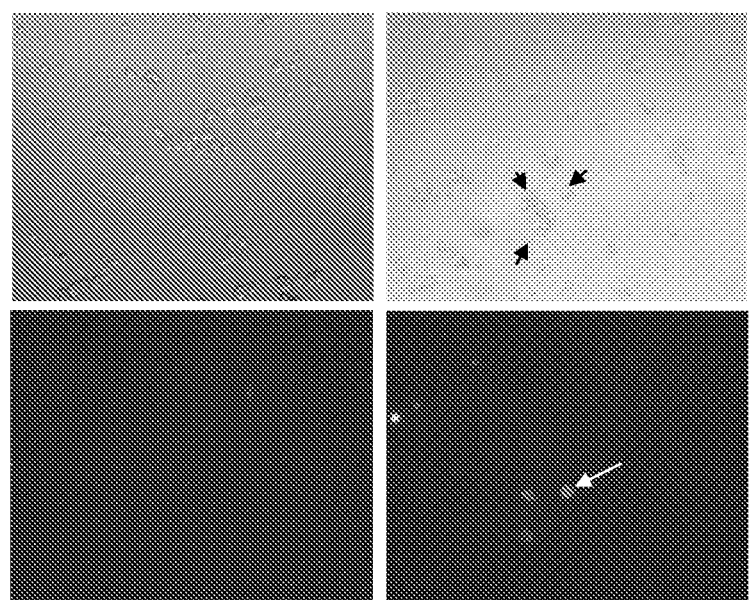
FIG. 1 shows an endosialin-specific binding by in-out antibody ES-1 by immunohistochemistry. Antibodies can be detected by western blot, ELISA using purified antigen, crude antigen, membrane preps or whole cells as well as immunostaining Shown is an immunostaining identifying antibody that can specifically bind to endosialin antigen. Immunostainings can be formatted with purified, semi-purified, membrane preps or whole cells expressing endosialin. Shown here are whole cells. Upper panels are whole field analysis of cells under phase contrast. Lower panels are same field of cells using fluorescein-labeled secondary antibody of cells stained with ES-1 or isotype antibody.

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include Ausubel et al. CURRENT PROTOCOLS IN MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, New York (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

Each range recited herein includes all combinations and sub-combinations of ranges, as well as specific numerals contained therein.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The invention provides methods for inhibiting the growth of endosialin-positive cells using in-out antibodies that specifically bind to endosialin, preferably mammalian endosialin, more preferably human endosialin (SEQ ID NOs:1 (nucleotide) and 2 (amino acid)). The methods of the invention may be used to modulate the growth of endosialin-positive cells to treat the progression of cancer, inflammation and/or neovascular disease in mammals, including humans. The cells that may be inhibited include all cells that have an increased expression of endosialin in relation to normal human tissues as well as endosialin-expressing leukocytes that may participate in neovascularization.

Without wishing to be bound by any particular theory of operation, it is believed that increased expression of endosialin in cancer tissue results in an increased cell surface expression of the membrane-bound form on the surface of the endothelial cells in the tumor. Therefore, cancer tissues have an increased expression of endosialin-expressing vessels and stromal cells relative to normal tissues. Thus, endosialin-positive cells are an ideal target for antibody therapy in cancer. Similarly, it is believed that increased endosialin expression in neovascular disease results in an increased cell surface expression of the membrane-bound form of the protein on the cell surface. Endosialin-positive cells are thus also an ideal target for antibody therapy in neovascular disease.

As used herein, the term "epitope" refers to the portion of an antigen to which an antibody specifically binds.

As used herein, the term "conformational epitope" refers to a discontinuous epitope formed by a spatial relationship between amino acids of an antigen other than an unbroken series of amino acids.

As used herein, the terms "immune effector activity," "immune effector effect," and "immune effector function" refer to the ability of an antibody to kill cells by antibody-dependent cellular cytotoxicity (ADCC) or complement-dependent cytotoxicity (CDC).

As used herein, the term "in-out antibody" refers to an antibody that can internalize within an antigen-presenting cell and, if not internalized, elicits an immune-effector activity.

As used herein, the phrase "in the alternative" when referring to the ability of an antibody to internalize or elicit an immune effector activity means that the antibody has the ability to both internalize and elicit an immune effector activity but cannot do both simultaneously.

As used herein, the term "inhibition of growth of cells in vitro" with reference to, for example, dysplastic or neovascular cells, means a decrease in the number of cells, in culture, by about 5%, preferably about 10%, more preferably about 20%, more preferably about 30%, more preferably about 40%, more preferably about 50%, more preferably about 60%, more preferably about 70%, more preferably about 80%, more preferably about 90%, and most preferably about 100%. In vitro inhibition of tumor cell growth may be measured by assays known in the art.

As used herein, the term "inhibition of growth of cells in vivo" with reference to, for example, dysplastic or neovascular cells, means a decrease in the number of cells in an organism by about 5%, preferably about 10%, more preferably about 20%, more preferably about 30%, more preferably about 40%, more preferably about 50%, more preferably about 60%, more preferably about 70%, more preferably about 80%, more preferably about 90%, and most preferably about 100%. In vivo modulation of cell growth may be measured by assays known in the art.

As used herein, "dysplastic cells" refer to cells that exhibit abnormal growth. Examples of abnormal growth properties include but are not limited to growth in soft agar, lack of contact inhibition, failure to undergo cell cycle arrest in the absence of serum, and formation of tumors when injected into immuno-compromised mice Dysplastic cells include, but are not limited to tumors, hyperplasia, and the like.

As used herein, "neovascular cells" refer to cells that are associated with tumor stroma, tumor vessels, inflammatory vessels, and vessels of neovascular diseases including eye disease.

The term "preventing" refers to decreasing the probability that an organism contracts or develops an abnormal condition such as dysplasia or a neovascular disease.

The term "treating" refers to having a therapeutic effect and at least partially alleviating or abrogating an abnormal condition such as dysplasia or a neovacular disease in the organism. Treating includes, for example, maintenance of inhibited tumor growth, induction of remission, improved vision, slowed loss of vision, and delayed vision impairment.

"Therapeutic effect" refers to the reduction, elimination, or prevention of a disease or abnormal condition, symptoms thereof, or side effects thereof in the subject. "Effective amount" refers to an amount necessary to produce a desired effect. A "therapeutically effective amount" means the amount that, when administered to a subject for treating a disease, condition or disorder, is sufficient to effect treatment for that disease A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) of growth of tumor cells in vivo (c) promotion of cell death; (d) inhibition of degeneration; (e) relieving to some extent one or more of the symptoms associated with the abnormal condition; (f) enhancing the function of a population of cells; (g) inhibiting cell binding to a matrix or ligand; (h) altering cell migration; and (i) altering cell response to therapy. The antibodies and derivatives thereof described herein effectuate the therapeutic effect alone or in combination with conjugates or additional components of the compositions of the invention.

As used herein, the term "inhibits the progression of neoplastic disease" refers to an activity of a treatment that slows the modulation of neoplastic disease toward end-stage cancer in relation to the modulation toward end-stage disease of untreated cancer cells.

As used herein, the term "inhibits neovascular disease" refers to an activity of a treatment that slows or reverses disease within neovascular tissues.

As used herein, the term "neovascular tissue" refers to disease tissue that may respond to therapy targeted at endothelial cells and/or endothelial precursors including tissues affected with inflammation, eye disease and cancer.

As used herein, the term "neoplastic disease" refers to a condition marked by abnormal proliferation of cells of a tissue such as cancer.

As used herein the term "biomolecule" refers to any molecule that can be conjugated to, coadministered with, administered before or after administering the antibody, or otherwise used in association with the antibody of the invention. Biomolecules include, but are not limited to, enzymes, proteins, peptides, amino acids, nucleic acids, lipids, carbohydrates, and fragments, homologs, analogs, or derivatives, and combinations thereof. Examples of biomolecules include but are not limited to interleukin-2, interferon alpha, interferon beta, interferon gamma, rituxan, zevalin, herceptin, erbitux, and avastin. The biomolecules can be native, recombinant, or synthesized, and may be modified from their native form with, for example, glycosylations, acetylations, phosphorylations, myristylations, and the like. The term biomolecule as it is used herein is not limited to naturally occurring molecules, and includes synthetic molecules having no biological origin.

As used herein, the term "cytotoxic" or "cytostatic" agent refers to an agent that reduces the viability or proliferative potential of a cell. Cytotoxic or cytostatic agents can function in a variety of ways to reduce cell viability or proliferation, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Specific examples of chemotherapeutic agents include, but are not limited to, radionuclides, pokeweed antiviral protein, abrin, ricin and each of their A chains, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxol, tarceva, avastin, mitomycin, modified *Pseudomonas* enterotoxin A, calicheamicin, 5-fluorouracil, cyclophosphamide and certain cytokines such as TNF-alpha and TNF-beta.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "nucleic acid" or "polynucleotide sequence" refers to a single or double-stranded polymer of deoxyribonucleotide or ribonucleotide bases read from the 5' to the 3' end. Nucleic acids can also include modified nucleotides that permit correct read through by a polymerase and do not alter expression of a polypeptide encoded by that nucleic acid, including, for example, conservatively modified variants.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Polypeptides of the invention, including antibodies of the invention, include conservatively modified variants. One of skill will recognize that substitutions, deletions or additions to a nucleic acid, peptide, polypeptide, or protein sequence which alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (33). The term "conservative substitution" also includes the use of a substituted amino acid in place of an unsubstituted parent amino acid provided that such a polypeptide also displays the requisite binding activity.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones but retain the same basic chemical structure as a naturally occurring amino acid. "Amino acid mimetic" refers to a chemical compound having a structure that is different from the general chemical structure of an amino acid but that functions in a manner similar to a naturally occurring amino acid.

Amino acids can be referred to herein by either their commonly known three letter symbols or by the one-letter symbols recommended by the IUPAC-IUB Biochemical Nomenclature Commission (see Table 1 below). Nucleotides, likewise, can be referred to by their commonly accepted single-letter codes.

TABLE 1

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-aspragine |
| C | Cys | L-cysteine |

It should be noted that all amino acid sequences are represented herein by formulae whose left to right orientation is in the conventional direction of amino-terminus to carboxy-terminus.

As used herein, the term "in vitro" or "ex vivo" refers to an artificial environment and to processes or reactions that occur within an artificial environment, for example, but not limited to, test tubes and cell cultures. The term "in vivo" refers to a natural environment (e.g., an animal or a cell) and to processes or reactions that occur within a natural environment.

"Pharmaceutically acceptable," "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

The term "pharmaceutically acceptable carrier" refers to reagents, excipients, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include gases, liquids, and semi-solid and solid materials.

Except when noted, "subject" or "patient" are used interchangeably and refer to mammals such as human patients and non-human primates, as well as experimental animals such as rabbits, dogs, cats, rats, mice, and other animals. Accordingly, "subject" or "patient" as used herein means any mammalian patient or subject to which the compositions of the invention can be administered. In some embodiments of the present invention, the patient will be suffering from an infectious or inflammatory disease. In some embodiments of the present invention, the patient will have been diagnosed with cancer. In an exemplary embodiment of the present invention, to identify candidate patients for treatment according to the invention, accepted screening methods are employed to determine the status of an existing disease or condition in a subject or risk factors associated with a targeted or suspected disease or condition. These screening methods include, for example, examinations to determine whether a subject is suffering from an infectious disease, an inflammatory disease, or cancer. These and other routine methods allow the clinician to select subjects in need of therapy.

"Therapeutic compound" as used herein refers to a compound useful in the prophylaxis or treatment of a disease or condition such as cancer.

"Concomitant administration," "concurrent administration," or "co-administration" as used herein includes administration of the active agents (e.g., MAbs, chemotherapeutic agents, biomolecules), in conjunction or combination, together, or before or after each other. The multiple agent(s) may be administered by the same or by different routes, simultaneously or sequentially, as long as they are given in a manner sufficient to allow all agents to achieve effective concentrations at the site of action. A person of ordinary skill in the art would have no difficulty determining the appropriate timing, sequence, and dosages of administration for particular drugs and compositions of the present invention.

"Immunoglobulin" or "antibody" is used broadly to refer to both antibody molecules and a variety of antibody-derived molecules and includes any member of a group of glycoproteins occurring in higher mammals that are major components of the immune system. The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')2, and Fv), so long as they exhibit the desired biological activity. An immunoglobulin molecule includes antigen binding domains, which each include the light chains and the end-terminal portion of the heavy chain, and the Fc region, which is necessary for a variety of functions, such as complement fixation. There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM, respectively. As used herein "immunoglobulin" or "antibody" includes all subclasses of alpha, delta, epsilon, gamma, and mu and also refers to any natural (e.g., IgA and IgM) or synthetic multimers of the four-chain immunoglobulin structure. Antibodies non-covalently, specifically, and reversibly bind an antigen. The term "monoclonal antibody" as used herein refers to an antibody obtained from a population of substantially homogeneous antibodies, i.e., the individual antibodies comprising the population are identical except for possible naturally occurring mutations that can be present in minor amounts. For example, monoclonal antibodies may be produced by a single clone of antibody-producing cells. Unlike polyclonal antibodies, monoclonal antibodies are monospecific (e.g., specific for a single epitope of a single antigen). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., *Nature*, 256: 495, 1975, or can be made by recombinant DNA methods. The "monoclonal antibodies" can also be isolated from phage antibody libraries using the techniques described in Marks et al., *J. Mol. Biol.*, 222: 581-597, 1991, for example.

Antibody-derived molecules comprise portions of intact antibodies that retain antigen-binding specificity, and comprise, for example, at least one variable region (either a heavy chain or light chain variable region). Antibody-derived molecules, for example, include molecules such as Fab fragments, Fab' fragments, F(ab')2 fragments, Fd fragments, F(v) fragments, Fabc fragments, Fd fragments, Fabc fragments, Sc antibodies (single chain antibodies), diabodies, individual antibody light chains, individual antibody heavy chains, chimeric fusions between antibody chains and other molecules, heavy chain monomers or dimers, light chain monomers or dimers, dimers consisting of one heavy and one light chain, and the like. All classes of immunoglobulins (e.g., IgA, IgD, IgE, IgG and IgM) and subclasses thereof are included.

Antibodies can be labeled/conjugated to toxic or non-toxic moieties. Toxic moieties include, for example, bacterial toxins, viral toxins, radioisotopes, and the like. Antibodies can be labeled for use in biological assays (e.g., radioisotope labels, fluorescent labels) to aid in detection of the antibody. Antibodies can also be labeled/conjugated for diagnostic or therapeutic purposes, e.g., with radioactive isotopes that deliver radiation directly to a desired site for applications such as radioimmunotherapy (Garmestani et al., *Nucl. Med. Biol.*, 28: 409, 2001), imaging techniques and radioimmunoguided surgery or labels that allow for in vivo imaging or detection of specific antibody/antigen complexes. Antibodies may also be conjugated with toxins to provide an immunotoxin (see, Kreitman, R. J. *Adv. Drug Del. Rev.*, 31: 53, 1998).

With respect to antibodies, the term, "immunologically specific" refers to antibodies that bind to one or more epitopes of a protein of interest, but which do not substantially recognize and bind other molecules in a sample containing a mixed population of antigenic biological molecules.

"Chimeric" or "chimerized" antibodies (immunoglobulins) refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al., *Proc. Natl. Acad. Sci. U.S.A.*, 81: 6851-6855, 1984).

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321: 522-525, 1986; Reichmann et al., *Nature*, 332: 323-329, 1988; Presta, *Curr. Op. Struct. Biol.*, 2: 593-596, 1992.

"Fully human" refers to an immunoglobulin, such as an antibody, where the whole molecule is of human origin or consists of an amino acid sequence identical to a human form of the antibody.

"Hybridoma" refers to the product of a cell-fusion between a cultured neoplastic lymphocyte and a primed B- or T-lymphocyte which expresses the specific immune potential of the parent cell.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Various patents and other publications are cited herein and throughout the specification, each of which is incorporated by reference herein in its entirety.

Antibodies

The antibodies of the invention specifically bind an epitope, for example a conformational epitope, of endosialin and exhibit in-out activity (i.e., in the alternative, the ability to induce an immune effector activity and the ability to internalize in endosialin-positive cells). Endosialin to which the antibodies of the invention bind is preferably mammalian, more preferably human. Human endosialin is encoded by SEQ ID NO:1 and comprises an amino acid sequence of SEQ ID NO:2:

```
SEQ ID NO 1: cDNA of human endosialin/TEM1
   1 agtccggggg catcgcgatg ctgctgcgcc tgttgctggc ctgggcggcc gcagggccca
  61 cactgggcca ggacccctgg gctgctgagc cccgtgccgc ctgcggcccc agcagctgct
 121 acgctctctt cccacggcgc cgcaccttcc tggaggcctg gcgggcctgc cgcgagctgg
 181 ggggcgacct ggccactcct cggacccccg aggaggccca gcgtgtggac agcctggtgg
 241 gtgcgggccc agccagccgg ctgctgtgga tcgggctgca gcggcaggcc cggcaatgcc
 301 agctgcagcg cccactgcgc ggcttcacgt ggaccacagg ggaccaggac acggctttca
 361 ccaactgggc ccagccagcc tctggaggcc cctgcccggc ccagcgctgt gtggccctgg
 421 aggcaagtgg cgagcaccgc tggctggagg gctcgtgcac gctggctgtc gacggctacc
 481 tgtgccagtt tggcttcgag ggcgcctgcc cggcgctgca agatgaggcg ggccaggccg
 541 gcccagccgt gtataccacg cccttccacc tggtctccac agagtttgag tggctgccct
 601 tcggctctgt ggccgctgtg cagtgccagg ctggcagggg agcctctctg ctctgcgtga
 661 agcagcctga gggaggtgtg ggctggtcac gggctgggcc cctgtgcctg gggactggct
 721 gcagccctga caacgggggc tgcgaacacg aatgtgtgga ggaggtggat ggtcacgtgt
 781 cctgccgctg cactgagggc ttccggctgg cagcagacgg gcgcagttgc gaggacccct
 841 gtgcccaggc tccgtgcgag cagcagtgtg agcccggtgg gccacaaggc tacagctgcc
 901 actgtcgcct gggtttccgg ccagcggagg atgatccgca ccgctgtgtg gacacagatg
 961 agtgccagat tgccggtgtg tgccagcaga tgtgtgtcaa ctacgttggt ggcttcgagt
1021 gttattgtag cgagggacat gagctggagg ctgatggcat cagctgcagc cctgcagggg
1081 ccatgggtgc ccaggcttcc caggacctcg gagatgagtt gctggatgac ggggaggatg
1141 aggaagatga agacgaggcc tggaaggcct tcaacggtgg ctggacggag atgcctggga
1201 tcctgtggat ggagcctacg cagccgcctg actttgccct ggcctataga ccgagcttcc
1261 cagaggacag agagccacag atacccacc cggagcccac ctggccaccc ccgctcagtg
1321 cccccagggt ccctaccac tcctcagtgc tctccgtcac ccggcctgtg gtggtctctg
1381 ccacgcatcc cacactgcct tctgcccacc agcctcctgt gatccctgcc acacacccag
1441 ctttgtcccg tgaccaccag atccccgtga tcgcagccaa ctatccagat ctgccttctg
1501 cctaccaacc cggtattctc tctgtctctc attcagcaca gcctcctgcc caccagcccc
1561 ctatgatctc aaccaaatat ccggagctct tccctgccca ccagtccccc atgtttccag
```

-continued
```
1621 acacccgggt cgctggcacc cagaccacca ctcatttgcc tggaatccca cctaaccatg 1681 ccctctggt caccacctc ggtgcccagc taccccctca agcccagat gcccttgtcc 1741 tcagaaccca ggccacccag cttcccatta tcccaactgc ccagccctct ctgaccacca 1801 cctccaggtc cctgtgtct cctgccatc aaatctctgt gcctgctgcc acccagcccg 1861 cagccctccc caccctcctg ccctctcaga gccccactaa ccagacctca cccatcagcc 1921 ctacacatcc ccattccaaa gcccccaaa tccaaggga agatggcccc agtcccaagt 1981 tggccctgtg gctgccctca ccagctccca cagcagcccc aacagccctg ggggaggctg 2041 gtcttgccga gcacagccag agggatgacc ggtggctgct ggtggcactc ctggtgccaa 2101 cgtgtgtctt tttggtggtc ctgcttgcac tgggcatcgt gtactgcacc cgctgtggcc 2161 cccatgcacc caacaagcgc atcactgact gctatcgctg ggtcatccat gctgggagca 2221 agagcccaac agaacccatg ccccccaggg gcagcctcac aggggtgcag acctgcagaa 2281 ccagcgtgtg atggggtgca gacccccctc atggagtatg gggcgctgga cacatggccg 2341 gggctgcacc agggacccat gggggctgcc cagctggaca gatggcttcc tgctccccag 2401 gcccagccag ggtcctctct caaccactag acttggctct caggaactct gcttcctggc 2461 ccagcgctcg tgaccaagga tacaccaaag cccttaagac ctcaggggc gggtgctggg 2521 gtcttctcca ataatgggg tgtcaacctt acccaaggaa aaaaaaaaa aaaaaa
```

SEQ ID NO 2: polypeptide sequence of human endosialin/TEM1
```
   1 mllrlllawa aagptlgqdp waaepraacg psscyalfpr rrtfleawra crelggdlat 61 prtpeeaqrv dslvgagpas rllwiglqrq arqcqlqrpl rgftwttgdq dtaftnwaqp 121 asggpcpaqr cvaleasgeh rwlegsctla vdgylcqfgf egacpalqde agqagpavyt 181 tpfhlvstef ewlpfgsvaa vqcqagrgas llcvkqpegg vgwsragplc lgtgcspdng 241 gcehecveev dghvscrcte gfrlaadgrs cedpcaqapc eqqcepggpq gyschcrlgf 301 rpaeddphrc vdtdecqiag vcqqmcvnyv ggfecycseg heleadgisc spagamgaqa 361 sqdlgdelld dgedeedede awkafnggwt empgilwmep tqppdfalay rpsfpedrep 421 qipypeptwp pplsaprvpy hssvlsvtrp vvvsathptl psahqppvip athpalsrdh 481 qipviaanyp dlpsayqpgi lsyshsaqpp ahqppmistk ypelfpahqs pmfpdtrvag 541 tqttthlpgi ppnhaplvtt lgaqlppqap dalvlrtqat qlpiiptaqp sltttsrspv 601 spahqisvpa atqpaalptl lpsqsptnqt spispthphs kapqipredg pspklalwlp 661 spaptaapta lgeaglaehs qrddrwllva llvptcvflv vllalgivyc trcgphapnk 721 ritdcyrwvi hagsksptep mpprgsltgv qtcrtsv
```

In some embodiments, the antibodies bind to the same epitope as FB5. In other embodiments, the antibodies bind to an epitope other than that bound by FB5.

Preferred antibodies, and antibodies suitable for use in the methods of the invention, include, for example, fully human antibodies, single chain antibodies, human antibody homologs, humanized antibody homologs, chimeric antibodies, chimeric antibody homologs, and monomers or dimers of antibody heavy or light chains or mixtures thereof The antibodies of the invention may include intact immunoglobulins of any isotype including types IgA, IgG, IgE, IgD, IgM (as well as subtypes thereof). The light chains of the immunoglobulin may be kappa or lambda.

The antibodies of the invention include portions of intact antibodies that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. Thus, antigen-binding fragments, as well as full-length dimeric or trimeric polypeptides derived from the above-described antibodies are themselves useful for exhibiting in-out activity.

It was found that the direct use of rodent monoclonal antibodies as human therapeutic agents led to human anti-rodent antibody ("HARA") responses which occurred in a significant number of patients treated with the rodent-derived antibody (Khazaeli, et al. (1994) *Immunother.* 15:42-52). Chimeric antibodies containing less rodent amino acid sequence were thought to circumvent the problem of eliciting an immune response in humans.

Chimeric antibodies may be produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al. describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) *Nature* 332:323-327 and Verhoeyen et al. (1988) *Science* 239:1534-1536.

As a non-limiting example, a method of performing CDR grafting may be performed by sequencing the mouse heavy and light chains of the antibody of interest that binds to the target antigen (e.g., endosialin) and genetically engineering the CDR DNA sequences and imposing these amino acid sequences to corresponding human V regions by site-directed mutagenesis. Human constant region gene segments of the desired isotype are added, and the chimeric heavy and light chain genes are co-expressed in mammalian cells to produce soluble antibody. A typical expression cell is a Chinese Hamster Ovary (CHO) cell. Other expression cells include HEK293 and myeloma cells. Suitable methods for creating the chimeric antibodies may be found, for example, in Jones et al. (1986) *Nature* 321:522-525; Riechmann (1988) *Nature* 332:323-327; Queen et al. (1989) *Proc. Nat. Acad. Sci. USA* 86:10029; and Orlandi et al. (1989) *Proc. Natl. Acad. Sci. USA* 86:3833.

Further refinement of antibodies to avoid the problem of HARA responses led to the development of "humanized antibodies." Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

Queen et al. (1989) *Proc. Nat. Acad. Sci. USA* 86:10029-10033 and WO 90/07861 describe the preparation of a humanized antibody. Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) *Biotechnology* 9:266-271.

The antibodies of the invention include derivatives that are modified, e.g., by the covalent attachment of any type of molecule to the antibody such that covalent attachment does not prevent the antibody from binding to its epitope. Examples of suitable derivatives include, but are not limited to glycosylated antibodies and fragments, acetylated antibodies and fragments, pegylated antibodies and fragments, phosphorylated antibodies and fragments, and amidated antibodies and fragments. The antibodies and derivatives thereof of the invention may themselves be derivatized by known protecting/blocking groups, proteolytic cleavage, linkage to a cellular ligand or other proteins, and the like. Further, the antibodies and derivatives thereof of the invention may contain one or more non-classical amino acids.

The antibodies of the invention include variants having single or multiple amino acid substitutions, deletions, additions, or replacements that retain the biological properties (e.g., internalization, binding affinity or avidity, or immune effector activity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, endosialin binding affinity or avidity, the ability to internalize, and immune effector activity.

The invention also encompasses fully human antibodies such as those derived from peripheral blood mononuclear cells of endosialin-linked cancer patients. Such cells may be fused with myeloma cells, for example to form hybridoma cells producing fully human antibodies against endosialin.

The antibodies and derivatives thereof of the invention have binding affinities that include a dissociation constant ($K_d$) of less than $1\times10^{-2}$. In some embodiments, the $K_d$ is less than $1\times10^{-3}$. In other embodiments, the $K_d$ is less than $1\times10^{-4}$. In some embodiments, the $K_d$ is less than $1\times10^{-5}$. In still other embodiments, the $K_d$ is less than $1\times10^{-6}$. In other embodiments, the $K_d$ is less than $1\times10^{-7}$. In other embodiments, the $K_d$ is less than $1\times10^{-8}$. In other embodiments, the $K_d$ is less than $1\times10^{-9}$. In other embodiments, the $K_d$ is less than $1\times10^{-10}$. In still other embodiments, the $K_d$ is less than $1\times10^{-11}$. In some embodiments, the $K_d$ is less than $1\times10^{-12}$. In other embodiments, the $K_d$ is less than $1\times10^{-13}$. In other embodiments, the $K_d$ is less than $1\times10^{-14}$. In still other embodiments, the $K_d$ is less than $1\times10^{-15}$.

Without wishing to be bound by any particular theory of operation, it is believed that the antibodies of the invention are particularly useful to bind endosialin due to an increased avidity of the antibody as both "arms" of the antibody (Fab fragments) bind to separate endosialin molecules. This leads to a decrease in the dissociation ($K_d$) of the antibody and an overall increase in the observed affinity ($K_D$). In addition, antibodies of this invention must bind to epitopes that allow for the internalization of the antibody-antigen complex. These are especially good features for targeting tumors and neovascular tissues as the antibodies of the invention will bind more tightly to tumor or neovascular tissue than normal tissue to attract immune cells for cytotoxicity and be capable of internalizing for delivery of conjugated agents for added therapeutic effects.

The antibodies of the invention may be used alone or with (e.g., coadministered or conjugated to) a biomolecule or chemotherapeutic agent such as a cytotoxic or cytostatic agent. In some embodiments, the chemotherapeutic agent is a radionuclide, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the chemotherapeutic agent is a toxin or cytotoxic drug, including but not limited to ricin, modified *Pseudomonas* enterotoxin A, calicheamicin, adriamycin, 5-fluorouracil, and the like. Methods of conjugation of antibodies and antibody fragments to such agents are known in the literature.

Also included in the invention are cells producing the in-out antibodies of the invention. The antibody-producing cells of the invention may be bacterial, yeast, insect, and animal cells, preferably, mammalian cells. For example, the antibody-producing cells of the invention include insect cells, such as for example, *Spodoptera frugiperda* cells; yeast cells, such as, for example, *Saccharomyces cerevisiae* and *Schizosaccharomyces pombe* cells; and mammalian cells such as, for example Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK cells, mouse sertoli cells, human cervical carcinoma cells, buffalo rat liver cells, human lung cells, human liver cells, mouse mammary tumor cells, TRI cells, MRC 5 cells, and FS4 cells. Antibody-producing cells have been placed with the Amer. Type Cult. Coll. (10801 University Blvd., Manassas, Va. 20110-2209) on Apr. 24, 2006 and have been assigned Access. No. PTA-7554. Examples of in-out antibodies of the invention are antibodies produced by such cells.

Nucleic Acids

The invention also includes nucleic acids encoding the heavy chain and/or light chain of the anti-endosialin antibodies of the invention. "Nucleic acid" or a "nucleic acid molecule" as used herein refers to any DNA or RNA molecule, either single- or double-stranded and, if single-stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. In some embodiments of the invention, nucleic acids are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG software program. Nucleic acids of the invention also include complementary nucleic acids. In some instances, the sequences will be fully complementary (no mismatches) when aligned. In other instances, there may be up to about a 20% mismatch in the sequences.

Nucleic acids of the invention also include fragments of the nucleic acids of the invention. A "fragment" refers to a nucleic acid sequence that is preferably at least about 10 nucleic acids in length, more preferably about 40 nucleic acids, and most preferably about 100 nucleic acids in length. A "fragment" can also mean a stretch of at least about 100 consecutive nucleotides that contains one or more deletions, insertions, or substitutions. A "fragment" can also mean the whole coding sequence of a gene and may include 5' and 3' untranslated regions.

Nucleic acids of the invention can be cloned into a vector. A "vector" is a replicon, such as a plasmid, cosmid, bacmid, phage, artificial chromosome (BAC, YAC) or virus, into which another genetic sequence or element (either DNA or RNA) may be inserted so as to bring about the replication of the attached sequence or element. A "replicon" is any genetic element, for example, a plasmid, cosmid, bacmid, phage, artificial chromosome (BAC, YAC) or virus, that is capable of replication largely under its own control. A replicon may be either RNA or DNA and may be single- or double-stranded. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

Nucleic acids encoding antibodies of the invention may be recombinantly expressed. The expression cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK cells, mouse sertoli cells, human cervical carcinoma cells, buffalo rat liver cells, human lung cells, human liver cells, mouse mammary tumor cells, TRI cells, MRC 5 cells, and FS4 cells.

Nucleic acids of the invention may be introduced into a cell by transfection, for example. Recombinantly expressed antibodies may be recovered from the growth medium of the cells, for example.

Methods of Producing in-Out Antibodies to Endosialin
Immunizing Animals

The invention also provides methods of producing in-out monoclonal antibodies that specifically bind to endosialin. Endosialin may be purified from cells or from recombinant systems using a variety of well-known techniques for isolating and purifying proteins. For example, but not by way of limitation, endosialin may be isolated based on the apparent molecular weight of the protein by running the protein on an SDS-PAGE gel and blotting the proteins onto a membrane. Thereafter, the appropriate size band corresponding to endosialin may be cut from the membrane and used as an immunogen in animals directly, or by first extracting or eluting the protein from the membrane. As an alternative example, the protein may be isolated by size-exclusion chromatography alone or in combination with other means of isolation and purification. Other means of purification are available in such standard reference texts as Zola, MONOCLONAL ANTIBODIES: PREPARATION AND USE OF MONOCLONAL ANTIBODIES AND ENGINEERED ANTIBODY DERIVATIVES (BASICS: FROM BACKGROUND TO BENCH) Springer-Verlag Ltd., New York, 2000; BASIC METHODS IN ANTIBODY PRODUCTION AND CHARACTERIZATION, Chapter 11, "Antibody Purification Methods," Howard and Bethell, Eds., CRC Press, 2000; ANTIBODY ENGINEERING (SPRINGER LAB MANUAL.), Kontermann and Dubel, Eds., Springer-Verlag, 2001.

One strategy for generating in-out antibodies against endosialin involves immunizing animals with cells expressing endosialin. Animals so immunized will produce antibodies against the protein. Standard methods are known for creating monoclonal antibodies including, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

Antibodies of the invention may be produced in vivo or in vitro. For in vivo antibody production, animals are generally immunized with an immunogenic portion of endosialin. The antigen or antigen-positive cell is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and corynebacterium parvum. Such adjuvants are also well known in the art.

Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-endosialin antibodies using appropriate screening assays as described below, for example.

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays such as those described below, may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art. Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

In-out antibodies against endosialin may also be prepared in vitro using a variety of techniques known in the art. For example, but not by way of limitation, fully human monoclonal antibodies against endosialin may be prepared by using in vitro-primed human splenocytes (Boerner et al. (1991) *J. Immunol.* 147:86-95).

Alternatively, for example, the antibodies of the invention may be prepared by "repertoire cloning" (Persson et al. (1991) *Proc. Nat. Acad. Sci. USA* 88:2432-2436; and Huang and Stollar (1991) *J. Immunol. Methods* 141:227-236). Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, in-out antibodies against endosialin are formed by in vitro immunization of peripheral blood mononuclear cells ("PBMCs"). This may be accomplished by any means known in the art, such as, for example, using methods described in the literature (Zafiropoulos et al. (1997) *J. Immunological Methods* 200:181-190).

Another strategy for generating in-out antibodies against endosialin involves immunizing animals with peptides corresponding to regions of the membrane bound form of endosialin that allow for internalization of antibodies that retain robust immune effector activity. Animals so immunized will produce antibodies against the protein. Standard methods are known for creating monoclonal antibodies including, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

In one embodiment of the invention, the procedure for in vitro immunization is supplemented with directed evolution of the hybridoma cells in which a dominant negative allele of a mismatch repair gene such as PMS1, PMS2, PMS2-134, PMSR2, PMSR3, MLH1, MLH2, MLH3, MLH4, MLHS, MLH6, PMSL9, MSH1, and MSH2 is introduced into the hybridoma cells after fusion of the splenocytes, or to the myeloma cells before fusion. Cells containing the dominant negative mutant will become hypermutable and accumulate mutations at a higher rate than untransfected control cells. A pool of the mutating cells may be screened for clones that produce higher affinity antibodies, or that produce higher titers of antibodies, or that simply grow faster or better under certain conditions. The technique for generating hypermutable cells using dominant negative alleles of mismatch repair genes is described in U.S. Pat. No. 6,146,894, issued Nov. 14, 2000. Alternatively, mismatch repair may be inhibited using the chemical inhibitors of mismatch repair described by Nicolaides et al. in WO 02/054856 "Chemical Inhibitors of Mismatch Repair" published Jul. 18, 2002. The technique for enhancing antibodies using the dominant negative alleles of mismatch repair genes or chemical inhibitors of mismatch repair may be applied to mammalian expression cells expressing cloned immunoglobulin genes as well. Cells expressing the dominant negative alleles can be "cured" in that the dominant negative allele can be turned off, if inducible, eliminated from the cell and the like such that the cells become genetically stable once more and no longer accumulate mutations at the abnormally high rate.

Screening for in-Out Antibodies

Screening for in-out antibodies that specifically bind to endosialin may be accomplished using an enzyme-linked immunosorbent assay (ELISA), by screening antibodies for immune effector activity, and/or by assaying for internalization. Antibodies exhibiting immune effector activity may be identified using a standard immune effector assay to monitor antibody-dependent cellular cytotoxicity (ADCC) or complement-dependent cytotoxicity (CDC). Antibodies that can be internalized can be identified by conjugating the antibody with a detectable label, such as a fluorochrome or prodrug, to monitor ability to internalize by visualization or toxicity. One or more of these assays (ELISA, immune effector assay, and internalization assay) may be performed in any order to identify in-out antibodies of the invention.

For example, the ELISA may comprise coating microtiter plates with immunizing antigen (whole protein or peptides). Antibodies from positively reacting clones can be screened for reactivity in an ELISA-based assay to endosialin. Clones that produce antibodies that are reactive to endosialin are selected for further expansion and development. Confirmation of endosialin-reactive antibodies exhibiting in-out activity may be accomplished, for example, using a standard immune effector assay to monitor antibody-dependent cellular cytotoxicity (ADCC) or complement-dependent cytotoxicity (CDC). Endosialin-specific antibodies exhibiting immune effector activity can then be conjugated with a fluorochrome or prodrug to monitor ability to internalize by visualization or toxicity that occurs when prodrug is internalized and liberated from the antibody leading to the presence of the toxin.

Pharmaceutical Compositions of Antibodies

Another aspect of the invention features a pharmaceutical composition of anti-endosialin antibodies of the invention. The pharmaceutical compositions may be used to inhibit or reduce growth of endosialin-positive cells in a patient. In certain embodiments, the pharmaceutical composition is formulated for administration by injection or infusion.

Pharmaceutical compositions of the invention may further comprise one or more biomolecules or chemotherapeutic agents. In some embodiments, the antibody is conjugated to the biomolecule or chemotherapeutic agent. Suitable chemotherapeutic agents include but are not limited to a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like.

Pharmaceutical compositions of the invention may be formulated with a pharmaceutically acceptable carrier or medium. Suitable pharmaceutically acceptable carriers include water, PBS, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences ($17^{th}$ Ed., Mack Pub. Co., Easton, Pa.).

Kits

According to yet another aspect of the invention, a kit is provided for inhibiting or reducing growth of endosialin-positive cells in vivo or in vitro. Also provided are kits for identifying the presence of endosialin-positive cells in vitro or in vivo.

The kits of the invention comprise antibody or an antibody composition of the invention and instructions for using the kit in a method for inhibiting or reducing growth of endosialin-positive cells in vitro or in vivo or in a method for identifying the presence of endosialin-positive cells, for example, in a biological sample. The kit may comprise at least one biomolecule or chemotherapeutic agent. The kit may comprise at least one diagnostic reagent. An example of a diagnostic reagent is a detectable label, for example but not limited to a radioactive, fluorescent, or chromophoric agent (e.g., $^{111}$In-DOTA). The detectable label may comprise an enzyme. The kit may comprise instructions and/or means for administering the antibody or antibody composition, for example, by injection or infusion.

Methods of Detecting an Endosialin-Positive Cell

The methods of the invention include methods of detecting cells, such as dysplastic or neovascular cells, presenting endosialin on the surface, including but not limited to ovarian, pancreatic, or lung cancer cells. The method may be performed in vitro on a biological sample or in vivo. Methods of detecting endosialin-positive cells according to the invention comprise contacting anti-endosialin antibody of the invention with a biological sample or administering anti-endosialin antibody of the invention to a patient, wherein the antibody is labeled with a detectable label, for example but not limited to a radioactive, fluorescent, or chromophoric agent (e.g., $^{111}$In-DOTA), and determining binding of the antibody to cells. The detectable label may be an enzyme.

Methods of Reducing the Growth of Endosialin-Positive Cells

The in-out anti-endosialin antibodies of the invention are suitable for use in reducing the growth of endosialin-positive cells in vitro or in vivo. The methods of the invention are suitable for use in humans and non-human animals identified as having a neoplastic or neovascular condition associated with tissue containing cells expressing endosialin, preferably cells demonstrating increased expression of endosialin. Non-human animals which benefit from the invention include pets, exotic (e.g., zoo animals) and domestic livestock. Preferably the non-human animals are mammals.

The invention is suitable for use in a human or animal patient that is identified as having a dysplastic disorder or neovascular disease that is marked by increased expression of endosialin in the neoplasm or neovascular tissue in relation to normal tissues. Once such a patient is identified as in need of treatment for such a condition, the method of the invention may be applied to effect treatment of the condition. Dysplastic or neovascular tissues that may be treated include, but are not limited to ovary, breast, colon, liver, brain, lung, pancreas, bone joints, bone, eye, nose, and prostate.

The antibodies and derivatives thereof for use in the invention may be administered orally in any acceptable dosage form such as capsules, tablets, aqueous suspensions, solutions or the like. The antibodies and derivatives thereof may also be administered parenterally. That is via the following routes of administration: subcutaneous, intravenous, intramuscular, intra-articular, intra-synovial, intrasternal, intranasal, topically, intrathecal, intrahepatic, intralesional, and intracranial injection or infusion techniques. Generally, the antibodies and derivatives will be provided as an intramuscular or intravenous injection.

The antibodies and derivatives of the invention may be administered alone or with a pharmaceutically acceptable carrier, including acceptable adjuvants, vehicles and excipients.

The antibodies of the invention may be administered before, after, or simultaneously with another therapeutic or diagnostic agent. For example, the in-out antibodies of the invention may be administered alone or with a cytotoxic agent such as but not limited to adriamycin, doxorubicin, gemcitabine, or 5-fluorouracil. The in-out antibodies of the invention may be administered alone or with a cytostatic agent such as but not limited to tarceva and avastin. The in-out antibodies and derivatives of the invention may be administered alone or with a vaccine agent. The in-out antibodies and derivatives of the invention may be administered alone or with another biomolecule such as but not limited to interleukin-2, interferon alpha, interferon beta, interferon gamma, rituxan, zevalin, herceptin, erbitux, avastin.

The in-out antibodies of the invention may be administered as a homogeneous mixture of unconjugated or conjugated antibody or as a heterogeneous mixture of unconjugated and conjugated in-out antibody.

The effective dosage will depend on a variety of factors and it is well within the purview of a skilled physician to adjust the dosage for a given patient according to various parameters such as body weight, the goal of treatment, the highest tolerated dose, the specific formulation used, the route of administration and the like. Generally, dosage levels of between about 0.001 and about 100 mg/kg body weight per day of the antibody or derivative thereof are suitable. In some embodiments, the dose will be about 0.1 to about 50 mg/kg body weight per day of the antibody or derivative thereof In other embodiments, the dose will be about 0.1 mg/kg body weight/day to about 20 mg/kg body weight/day. In still other embodiments, the dose will be about 0.1 mg/kg body weight/day to about 10 mg/kg body weight/day. Dosing may be as a bolus or an infusion. Dosages may be given once a day or multiple times in a day. Further, dosages may be given multiple times of a period of time. In some embodiments, the doses are given every 1-14 days. In some embodiments, the antibodies or derivatives thereof are given as a dose of about. 3 to 1 mg/kg i.p. In other embodiments, the antibodies of derivatives thereof are provided at about 5 to 12.5 mg/kg i.v. In still other embodiments, the antibodies or derivatives thereof are provided such that a plasma level of at least about 1 ug/ml is maintained.

Effective treatment may be assessed in a variety of ways. In one embodiment, effective treatment is determined by a slowed progression of tumor growth or reduced symptoms in neovascular diseased tissue. In other embodiments, effective treatment is marked by shrinkage of the tumor (i.e., decrease in the size of the tumor) or return of normal function in neovascular tissue. In other embodiments, effective treatment is marked by inhibition of metastasis of the tumor or improved normal function of the neovascular tissue. In still other embodiments, effective therapy is measured by increased well-being of the patient including such signs as weight gain, regained strength, decreased pain, improved eye sight, thriving, and subjective indications from the patient of better health and reduction of disease.

The following Examples are provided to illustrate the present invention, and should not be construed as limiting thereof

EXAMPLES

Example 1

In-Out Antibodies that can Bind to Endosialin

The monoclonal antibody ES-1 is a humanized antibody specific to endosialin. The antibody was shown to bind specifically to endosialin protein, cancer cells expressing endosialin, human embryonic endothelial cells, and leukocytes. To demonstrate endosialin-specific binding, whole cell ELISA were performed using endosialin-expressing cells in a 96-well format following methods used by those skilled in the art. Antibodies found to react by ELISA were further analyzed for endosialin binding using FACS analysis following the manufacturer's protocol. In-out antibodies can be identified by screening using immunohistochemistry (IHC). Use of IHC to detect antibodies that can bind to endosialin expressed on the cell surface was shown by immunohistochemistry of endothelial cells (ECs) that express endosialin. The anti-endosialin or normal IgG antibody was applied to ECs concentrations (0.5 ug/mL and 2.5 ug/mL). Phosphate-buffered saline [PBS (0.15M NaCl, pH 7.2)]+1% bovine serum albumin served as the diluent for the primary antibodies. Cells were plated onto slides and fixed in Tissue-Tek® O.C.T.

medium. Slides were stored below −70° C. until staining. Just prior to staining, slides were fixed for 10 seconds in 10% neutral-buffered formalin.

Slides were rinsed twice in phosphate-buffered saline (PBS [0.15M NaCl, pH 7.2]). Endogenous peroxidase was blocked by incubating the slides with the peroxidase solution provided in the Dako EnVision™ Kit for 5 minutes and rinsing twice in PBS (0.15M NaCl, pH 7.2). Next, the slides were treated with a protein block designed to reduce nonspecific binding for 20 minutes. The protein block was prepared as follows: PBS (0.15M NaCl, pH 7.2); 0.5% casein; 1% bovine serum albumin (BSA); and 1.5% normal goat serum. Following the protein block, the primary antibody (test article, negative control antibody, or none [buffer alone as the assay control]) was applied at room temperature for one hour. Next, the slides were rinsed two times with PBS (0.15M NaCl, pH 7.2), treated with the peroxidase-labeled goat anti-IgG polymer supplied in the Dako EnVision™ Kit for 30 minutes (EnVision™ polymer used at the concentration provided by manufacturer), rinsed two times with PBS (0.15M NaCl, pH 7.2), and treated with the substrate-chromogen (DAB) solution supplied in the Dako EnVision™ Kit for 8 minutes. All slides were rinsed in water, counterstained with hematoxylin, dehydrated and coverslipped for interpretation. Shown in FIG. 1 are representative data of the IHC analysis whereby endosialin expressing cells were positive for ES-1 binding in contrast to null cells.

Example 2

Immune Effector Activity of ES-1

Immune effector activity was assessed by standard antibody-dependent cellular cytotoxicity (ADCC) assays on the endosialin-expressing Lu cell line. Briefly, Lu target cells are seeded in flat-bottom 96-well microplates in complete growth medium (RPMI-1640 containing 10% FBS, 2 mM L-glutamine). The following day, the complete medium is replaced with 100 ul of CHO-CD serum-free medium (Sigma) and 50 ul of antibody-containing conditioned medium is added to target cells and incubated for 20 minutes at 37° C. Subsequently, 100 ul of serum-free medium containing $2 \times 10^5$ effector cells are added to each well and cells are incubated for 5-6 hours at 37° C., 5% $CO_2$. Effector cells are derived from human peripheral blood mononuclear cells (PBMCs), isolated from healthy donors (purchased from Interstate Blood Bank). Prior to use in ADCC, PBMCs are activated by seeding PBMCs at $2.5 \times 10^6$/ml in complete RPMI containing 10 ng/ml human recombinant interleukin 2 (R&D Systems) for 3 days at 37° C., 5% $CO_2$. Activated PBMCs are then added to OVCAR-3 cells at an effector:target cell ratio of 5:1 and cultures are incubated for 5-6 hours at 37° C., 5% $CO_2$. Supernatant is then collected from each well and transferred into ELISA plates and analyzed for ADCC as follows. ADCC is monitored by lactate dehydrogenase (LDH) release, an endogenous enzyme used to measure ADCC in standard assays. LDH is monitored by adding 100 ul of LDH substrate (Roche), a chemical that when converted by LDH is spectrophotometrically detectable at $OD_{490}$, to supernatant and incubated for 10 minutes at ambient temperature. LDH activity is proportional to the extent of the LDH enzyme released from lysed target cells. Optical density at 490 nm ($OD_{490}$) is obtained spectrophotometrically. 2% Triton X is added to effector cells alone as a "max" positive control, while target cells with PBMC and no antibody serve as the "spontaneous" negative control. LDH values are obtained and percent of cytotoxicity is determined with the formula: (sample value−spontaneous)/(max−spontaneous)×100%, where 'spontaneous'=target cell lysis in absence of effector cells, and 'max'=target cell lysis in the presence of 2% Triton. Non-specific cytotoxicity will be monitored using 100 ng/ml of normal human IgG1 antibody. The ratio obtained by dividing the % cytotoxicity by the concentration of the antibody for each well/clone (i.e. ratio=50(%)/100(ng/m1)=0.5) will be set as the criterion for selecting lead clones with potentially enhanced effector function.

Analysis of ES-1 shows the ability to enhance ADCC activity over cells incubated with control Ig or no antibody (FIG. 2). FIG. 2A illustrates non-denaturing Western blot of HMVEC cells showing the ability of ES-1 antibody to bind to endosialin while null melanoma cells were negative. The lower panel of FIG. 2B shows target HMVEC cells (referred to as target) incubated with human PBLs alone (0 lane); or with increasing amount of with ES-1 (right bar) or control Ig (normal IgG-left bar). Cell cultures were assayed for killing by monitoring for lactate dehydrogenase (LDH) release that occurs upon cell lysis. As shown, ES-1 has ADCC activity on endosialin-expressing cells. The upper panel of FIG. 2B shows human melanoma cells that are null for endosialin incubated with human PBLs alone (0 lane); or with increasing amount of with ES-1 (right bar) or control Ig (normal IgG-left bar). Cell cultures were assayed for killing by monitoring for lactate dehydrogenase (LDH) release that occurs upon cell lysis. As shown, ES-1 has no ADCC activity on endosialin null cells. These data support the finding that ES-1 has cytotoxic effects via immune effector function.

Example 3

ES-1 Antibody Internalization

Figure 3:
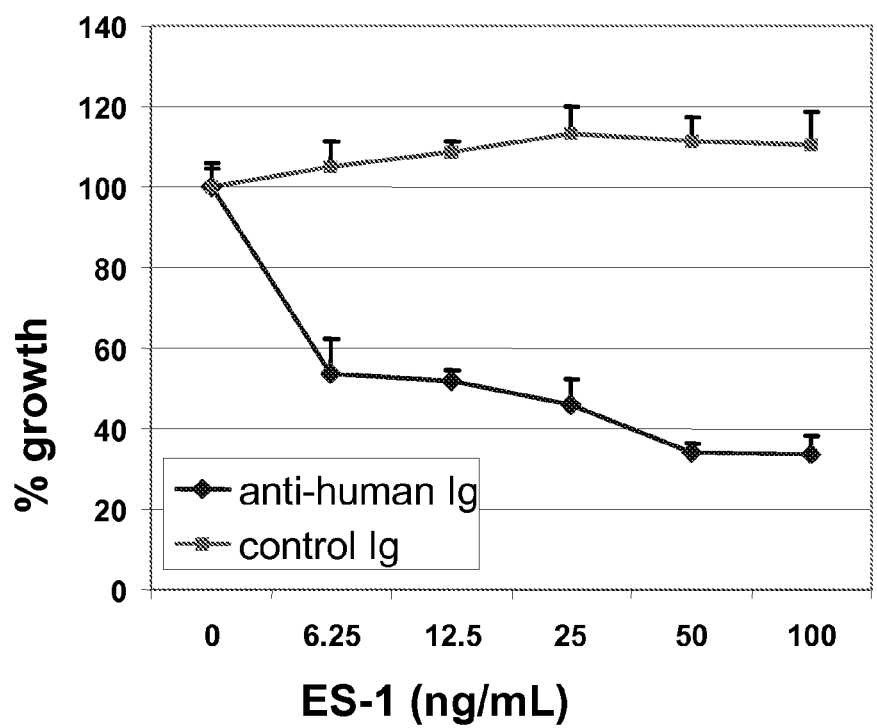
FIG. 3 shows the ability of ES-1 to internalize in endosialin-bearing cells. ES-1 internalizes in endosialin-expressing cells.

ES-1 internalizes when bound to endosialin-expressing cells. This finding is shown in FIG. 3 using the Hum-ZAP assay. Second immunotoxins are conjugations of a secondary antibody to the ribosome inactivating protein saporin. If the primary antibody being tested is internalized, the saporin is transported into the cell via its binding to the secondary antibody. Once internalized saporin separates from its IgG conjugate, it inhibits protein synthesis and ultimately causes cell death. Hum-ZAP (Advanced Targeting Systems, cat# IT-22) is a secondary chemical conjugate of affinity purified goat anti-human IgG (mw 210kDa) that recognizes human monoclonal antibodies. The control molecule, Goat IgG-SAP (Advanced Targeting Systems cat#IT-19) is a conjugate of normal goat IgG and saporin. Briefly, cells are plated into flat-bottom 96 well tissue culture plates at 2500/well in 80ul of RPMI 1640 with 10% FCS, 2.0 mM glutamine, 1.0 mM sodium pyruvate, and 0.1 mM MEM non-essential amino acids. Twenty-four hours later, 10 ul of primary antibodies ES-1 or MORAb-A92 are added along with 10 μl of Hum-ZAP or Goat IgG-SAP to bring the total volume to 100 μl. Experiments are set up with antibody titrations and include primary and secondary antibodies alone as control. Four days later, cell viability is evaluated using Promega CellTiter® Cytotoxicity Assay (cat# G3581) which reads viable cell number by spectrophotometry. All tests are performed in triplicate. Data is evaluated by comparing treated and untreated wells and results are expressed as percent of control. As shown in FIG. 3, ES-1 linked to saporin (diamond) kills Lu cells, which overexpress endosialin, in contrast to ES-1 antibody alone (not shown) while an isotype control antibody MORAb-A92 did not kill cells in conjugated toxin form (square). As control, cells not expressing endosialin were used and showed that ES-1 has no toxic effect in conjugated or unconjugated form (not shown). These data support the findings that ES-1 internalizes in endosialin-bearing cells.

What is claimed:

1. A method of inhibiting growth of endosialin-positive cells comprising administering to a subject having said cells a therapeutically effective amount of a humanized antibody that specifically binds to endosialin, or antigen-binding fragment thereof, comprising the variable domains of the antibody produced by the cells assigned ATCC accession no. PTA-7554, wherein said antibody or antigen-binding fragment is conjugated to a cytotoxic biomolecule or to a chemotherapeutic agent.

2. A method of treating colorectal cancer characterized by endosialin expression in a subject in need thereof, said method comprising administering to said subject a therapeutically effective amount of a humanized antibody that specifically binds to endosialin, or antigen-binding fragment thereof, comprising the variable domains of the antibody produced by the cells assigned ATCC accession no. PTA-7554, wherein said antibody or antigen-binding fragment is conjugated to a cytotoxic biomolecule or to a chemotherapeutic agent.

3. The method of claim 1 wherein said chemotherapeutic agent is cytotoxic.

4. The method of claim 2 wherein said chemotherapeutic agent is cytotoxic.

5. A method of inhibiting growth of endosialin-positive cells comprising administering to a subject having said cells a therapeutically effective amount of a humanized antibody that specifically binds to endosialin, or antigen-binding fragment thereof, comprising the variable domains of the antibody produced by the cells assigned ATCC accession no. PTA-7554, wherein said antibody or antigen-binding fragment comprises a portion of an immunoglobulin constant region (Fc) capable of eliciting complement dependent cytotoxic activity or antibody-dependent cellular cytotoxicity.

6. The method of claim 5 further comprising administering to said subject a biomolecule or chemotherapeutic agent.

7. The method of claim 6 wherein said antibody or antigen-binding fragment is conjugated to said biomolecule or said chemotherapeutic agent.

8. The method of claim 6 wherein said biomolecule or said chemotherapeutic agent is cytotoxic.

9. The method of claim 7 wherein said biomolecule or said chemotherapeutic agent is cytotoxic.

10. A method of treating colorectal cancer characterized by endosialin expression in a subject in need thereof, said method comprising administering to said subject a therapeutically effective amount of a humanized antibody that specifically binds to endosialin, o antigen-binding fragment thereof, comprising the variable domains of the antibody produced by the cells assigned ATCC accession no. PTA-7554, wherein said antibody or antigen-binding fragment comprises a portion of an immunoglobulin constant region (Fc) capable of eliciting complement dependent cytotoxic activity or antibody-dependent cellular cytotoxicity.

11. The method of claim 10 further comprising administering to said subject biomolecule or chemotherapeutic agent.

12. The method of claim 11 wherein said antibody or antigen-binding fragment is conjugated to said biomolecule or said chemotherapeutic agent.

13. The method of claim 11 wherein said biomolecule or said chemotherapeutic agent is cytotoxic.

14. The method of claim 12 wherein said biomolecule or said chemotherapeutic agent is cytotoxic.

* * * * *

SEQUENCE LISTING

<160> NUMBER OF SEQ ID NOS: 2

<210> SEQ ID NO 1
<211> LENGTH: 2576
<212> TYPE: DNA
<213> ORGANISM: Homo sapiens

<400> SEQUENCE: 1

```
agtccggggg catcgcgatg ctgctgcgcc tgttgctggc ctgggcggcc gcagggccca      60
cactgggcca ggacccctgg gctgctgagc cccgtgccgc ctgcggcccc agcagctgct     120
acgctctctt cccacggcgc cgcaccttcc tggaggcctg gcgggcctgc cgcgagctgg     180
ggggcgacct ggccactcct cggacccccg aggaggccca gcgtgtggac agcctggtgg     240
gtgcgggccc agccagccgg ctgctgtgga tcgggctgca gcggcaggcc cggcaatgcc     300
agctgcagcg cccactgcgc ggcttcacgt ggaccacagg ggaccaggac acggctttca     360
ccaactgggc ccagccagcc tctggaggcc cctgcccggc ccagcgctgt gtggccctgg     420
aggcaagtgg cgagcaccgc tggctggagg gctcgtgcac gctggctgtc gacggctacc     480
tgtgccagtt tggcttcgag ggcgcctgcc cggcgctgca agatgaggcg gccaggccg      540 gcccagccgt gtataccacg cccttccacc tggtctccac agagtttgag tggctgccct     600
tcggctctgt ggccgctgtg cagtgccagg ctggcagggg agcctctctg ctctgcgtga     660
agcagcctga gggaggtgtg ggctggtcac gggctgggcc cctgtgcctg gggactggct     720
gcagccctga caacggggc tgcgaacacg aatgtgtgga ggaggtggat ggtcacgtgt      780
cctgccgctg cactgagggc ttccggctgg cagcagacgg gcgcagttgc gaggaccct      840 gtgcccaggc tccgtgcgag cagcagtgtg agcccgtgg gccacaaggc tacagctgcc      900
actgtcgcct gggttttcgg ccagcggagg atgatccgca ccgctgtgtg dacacagatg      960
agtgccagat tgccggtgtg tgccagcaga tgtgtgtcaa ctacgttggt ggcttcgagt    1020
gttattgtag cgagggacat gagctggagg ctgatggcat cagctgcagc cctgcagggg    1080
ccatgggtgc ccaggcttcc caggacctcg agatgagttt gctggatgac ggggaggatg    1140
aggaagatga agacgaggcc tggaaggcct tcaacggtgg ctggacggag atgcctggga    1200
tcctgtggat ggagcctacg cagccgcctg actttgccct ggcctataga ccgagcttcc    1260
cagaggacag agagccacag atacccta cggagcccac ctggccaccc ccgctcagtg      1320
cccccagggt cccctaccac tcctcagtgc tctccgtcac ccggcctgtg gtggtctctg    1380
ccacgcatcc cacactgcct tctgcccacc agcctcctgt gatccctgcc acacacccag    1440
ctttgtcccg tgaccaccag atcccgtga tcgcagccaa ctatccagat ctgccttctg      1500
cctaccaacc cggtattctc tctgtctctc attcagcaca gcctcctgcc caccagcccc    1560
ctatgatctc aaccaaatat ccggagctct cccctgccca ccagtccccc atgtttccag    1620
acacccgggt cgctggcacc cagaccacca ctcatttgcc tggaatccca cctaaccatg    1680
cccctctggt caccaccctc ggtgcccagc taccccctca gcccagat gcccttgtcc       1740 tcagaaccca ggccacccag cttcccatta tcccaactgc ccagccctct ctgaccacca    1800
cctccaggtc cctgtgtctc ctgcccatc aaatctctgt gctgctgcc acccagcccg       1860 cagccctccc caccctcctg ccctctcaga gccccactaa ccagacctca cccatcagcc    1920
ctacacatcc ccattccaaa gccccccaaa tccaaggga agatggcccc agtcccaagt      1980
tggccctgtg gctgccctca ccagctccca cagcagcccc aacagccctg gggaggctg      2040
```

-continued

```
gtcttgccga gcacagccag agggatgacc ggtggctgct ggtggcactc ctggtgccaa    2100
cgtgtgtctt tttggtggtc ctgcttgcac tgggcatcgt gtactgcacc cgctgtggcc    2160
cccatgcacc caacaagcgc atcactgact gctatcgctg ggtcatccat gctgggagca    2220
agagcccaac agaacccatg ccccccaggg gcagcctcac aggggtgcag acctgcagaa    2280
ccagcgtgtg atggggtgca gaccccctc atggagtatg gggcgctgga cacatggccg     2340
gggctgcacc agggacccat ggggctgcc cagctggaca gatggcttcc tgctccccag      2400
gcccagccag ggtcctctct caaccactag acttggctct caggaactct gcttcctggc    2460
ccagcgctcg tgaccaagga tacaccaaag cccttaagac ctcaggggc gggtgctggg      2520 gtcttctcca ataaatgggg tgtcaacctt acccaaggaa aaaaaaaaa aaaaaa         2576
```

<210> SEQ ID NO 2
<211> LENGTH: 757
<212> TYPE: PRT
<213> ORGANISM: Homo sapiens

<400> SEQUENCE: 2

```
Met Leu Leu Arg Leu Leu Leu Ala Trp Ala Ala Gly Pro Thr Leu
1               5                   10                  15

Gly Gln Asp Pro Trp Ala Ala Glu Pro Arg Ala Ala Cys Gly Pro Ser
                20                  25                  30

Ser Cys Tyr Ala Leu Phe Pro Arg Arg Arg Thr Phe Leu Glu Ala Trp
            35                  40                  45

Arg Ala Cys Arg Glu Leu Gly Gly Asp Leu Ala Thr Pro Arg Thr Pro
        50                  55                  60

Glu Glu Ala Gln Arg Val Asp Ser Leu Val Gly Ala Gly Pro Ala Ser
65                  70                  75                  80

Arg Leu Leu Trp Ile Gly Leu Gln Arg Gln Ala Arg Gln Cys Gln Leu
                85                  90                  95

Gln Arg Pro Leu Arg Gly Phe Thr Trp Thr Thr Gly Asp Gln Asp Thr
            100                 105                 110

Ala Phe Thr Asn Trp Ala Gln Pro Ala Ser Gly Gly Pro Cys Pro Ala
        115                 120                 125

Gln Arg Cys Val Ala Leu Glu Ala Ser Gly Glu His Arg Trp Leu Glu
    130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
            180                 185                 190

Leu Pro Phe Gly Ser Val Ala Ala Val Gln Cys Gln Ala Gly Arg Gly
        195                 200                 205

Ala Ser Leu Leu Cys Val Lys Gln Pro Glu Gly Gly Val Gly Trp Ser
    210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Val Asp Gly His Val Ser Cys
                245                 250                 255

Arg Cys Thr Glu Gly Phe Arg Leu Ala Ala Asp Gly Arg Ser Cys Glu
            260                 265                 270

Asp Pro Cys Ala Gln Ala Pro Cys Glu Gln Gln Cys Glu Pro Gly Gly
        275                 280                 285
```

-continued

```
Pro Gln Gly Tyr Ser Cys His Cys Arg Leu Gly Phe Arg Pro Ala Glu
            290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                    325                 330                 335

Cys Ser Glu Gly His Glu Leu Glu Ala Asp Gly Ile Ser Cys Ser Pro
                340                 345                 350

Ala Gly Ala Met Gly Ala Gln Ala Ser Gln Asp Leu Gly Asp Glu Leu
                355                 360                 365

Leu Asp Asp Gly Glu Asp Glu Glu Asp Glu Asp Ala Trp Lys Ala
370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                    405                 410                 415

Asp Arg Glu Pro Gln Ile Pro Tyr Pro Glu Pro Thr Trp Pro Pro Pro
                    420                 425                 430

Leu Ser Ala Pro Arg Val Pro Tyr His Ser Ser Val Leu Ser Val Thr
                435                 440                 445

Arg Pro Val Val Ser Ala Thr His Pro Thr Leu Pro Ser Ala His
450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                    485                 490                 495

Gln Pro Gly Ile Leu Ser Val Ser His Ser Ala Gln Pro Pro Ala His
                500                 505                 510

Gln Pro Pro Met Ile Ser Thr Lys Tyr Pro Glu Leu Phe Pro Ala His
                515                 520                 525

Gln Ser Pro Met Phe Pro Asp Thr Arg Val Ala Gly Thr Gln Thr Thr
                530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                    565                 570                 575

Thr Gln Ala Thr Gln Leu Pro Ile Ile Pro Thr Ala Gln Pro Ser Leu
                580                 585                 590

Thr Thr Thr Ser Arg Ser Pro Val Ser Pro Ala His Gln Ile Ser Val
                595                 600                 605

Pro Ala Ala Thr Gln Pro Ala Ala Leu Pro Thr Leu Leu Pro Ser Gln
610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                    645                 650                 655

Leu Trp Leu Pro Ser Pro Ala Pro Thr Ala Ala Pro Thr Ala Leu Gly
                660                 665                 670

Glu Ala Gly Leu Ala Glu His Ser Gln Arg Asp Asp Arg Trp Leu Leu
                675                 680                 685

Val Ala Leu Leu Val Pro Thr Cys Val Phe Leu Val Val Leu Leu Ala
                690                 695                 700

Leu Gly Ile Val Tyr Cys Thr Arg Cys Gly Pro His Ala Pro Asn Lys
705                 710                 715                 720
```

```
Arg Ile Thr Asp Cys Tyr Arg Trp Val Ile His Ala Gly Ser Lys Ser
            725                 730                 735

Pro Thr Glu Pro Met Pro Pro Arg Gly Ser Leu Thr Gly Val Gln Thr
            740                 745                 750

Cys Arg Thr Ser Val
            755
```